US008119066B2

(12) United States Patent
Stock et al.

(10) Patent No.: US 8,119,066 B2
(45) Date of Patent: Feb. 21, 2012

(54) MULTIMODE READER

(75) Inventors: Daniel M. Stock, Gartenau (AT); Josef J. Atzler, Hallem (AT)

(73) Assignee: Molecular Devices, LLC, Sunnyvale, CA (US)

( * ) Notice: Subject to any disclaimer, the term of this patent is extended or adjusted under 35 U.S.C. 154(b) by 1175 days.

(21) Appl. No.: 11/351,181

(22) Filed: Feb. 8, 2006

(65) Prior Publication Data

US 2007/0183931 A1    Aug. 9, 2007

(51) Int. Cl.
  *G01N 21/00* (2006.01)
(52) U.S. Cl. ............... 422/82.05; 422/82.06; 422/82.07; 422/82.08; 436/164; 436/165; 436/166; 436/171; 436/172
(58) Field of Classification Search .................. None
  See application file for complete search history.

(56) References Cited

U.S. PATENT DOCUMENTS

| | | | |
|---|---|---|---|
| 3,806,259 A | 4/1974 | Boostrom et al. | |
| 6,200,531 B1 | 3/2001 | Liljestrand et al. | 422/52 |
| 6,310,687 B1 | 10/2001 | Stumbo et al. | 356/317 |
| 6,379,969 B1 | 4/2002 | Mauze et al. | 436/68 |
| 6,409,909 B1 | 6/2002 | Spichiger-Keller et al. | 205/777.5 |
| 6,517,777 B2 | 2/2003 | Liljestrand et al. | 422/52 |
| 6,580,081 B1 | 6/2003 | Thorwirth | |
| 6,795,189 B2 | 9/2004 | Booker et al. | 356/417 |
| 6,822,741 B2 | 11/2004 | Aronkytoet et al. | |
| 6,878,947 B2 | 4/2005 | Haberstroh | 250/458.1 |
| 6,891,618 B2 | 5/2005 | Harju et al. | 356/417 |
| 2002/0043626 A1 | 4/2002 | Booker et al. | 250/459.1 |
| 2002/0060791 A1 | 5/2002 | Stumbo et al. | 356/317 |
| 2002/0113213 A1 | 8/2002 | Aronkyto et al. | 250/458.1 |
| 2003/0042428 A1 | 3/2003 | Peukert et al. | 250/458.1 |
| 2003/0048445 A1 | 3/2003 | Tokhtuev et al. | |
| 2003/0048446 A1 | 3/2003 | Aronkyto et al. | 356/417 |
| 2003/0048447 A1 | 3/2003 | Harju et al. | 356/417 |
| 2003/0117628 A1 | 6/2003 | Harju et al. | 356/417 |
| 2003/0118477 A1 | 6/2003 | Liljestrand et al. | 422/52 |
| 2004/0057870 A1 | 3/2004 | Isaksson et al. | 422/52 |
| 2004/0120857 A1 * | 6/2004 | Smith et al. | 422/82.05 |
| 2005/0012252 A1 | 1/2005 | Yu et al. | 266/241 |
| 2005/0012929 A1 | 1/2005 | Booker et al. | 356/417 |
| 2005/0023445 A1 | 2/2005 | Horn et al. | |
| 2005/0062969 A1 | 3/2005 | Harju et al. | 356/417 |
| 2005/0063279 A1 | 3/2005 | Song et al. | 369/99 |
| 2005/0105080 A1 | 5/2005 | Landlinger | 356/73 |
| 2005/0109950 A1 | 5/2005 | King | |

FOREIGN PATENT DOCUMENTS

DE    4327752    2/1995

OTHER PUBLICATIONS

Office Action for CN 2007800047561, mailed Mar. 16, 2010.

* cited by examiner

*Primary Examiner* — Yelena G Gakh
*Assistant Examiner* — David Weisz
(74) *Attorney, Agent, or Firm* — Bella Fishman; David Glockler

(57) ABSTRACT

A cartridge and cartridge system for use in an apparatus for analyzing a sample are provided. The cartridge has one or more light sources and/or optical systems and other components that are specific for a certain type of application such as fluorescence, absorbance, or luminescence. The light source, optical systems, and other components for a specific application are housed in a single cartridge. The system has a plurality of cartridges for different applications for a multimode instrument. The cartridges are removably engaged with the apparatus in a "plug-in" format such that one cartridge may be removed from the apparatus and another cartridge may be easily installed.

72 Claims, 18 Drawing Sheets

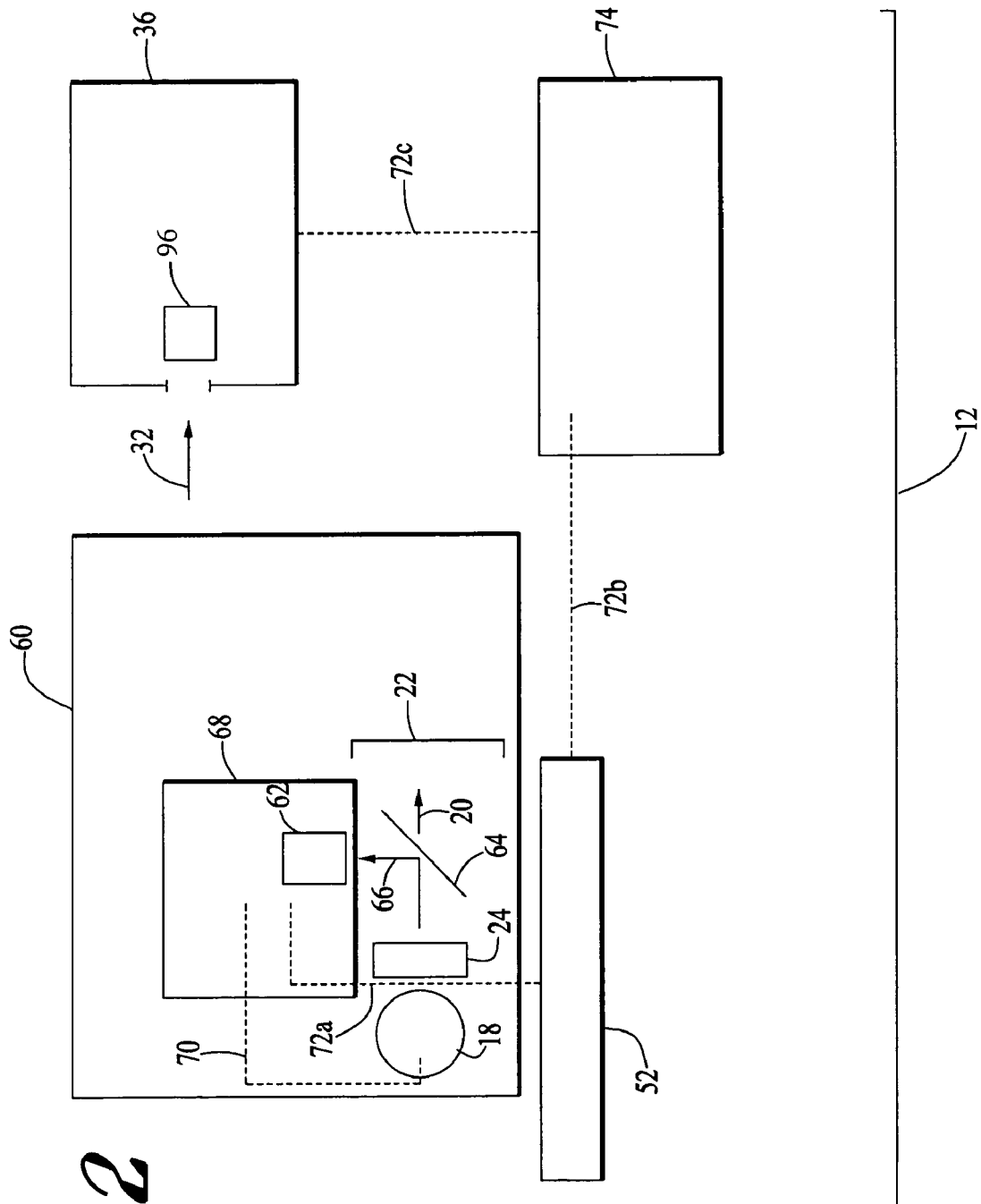

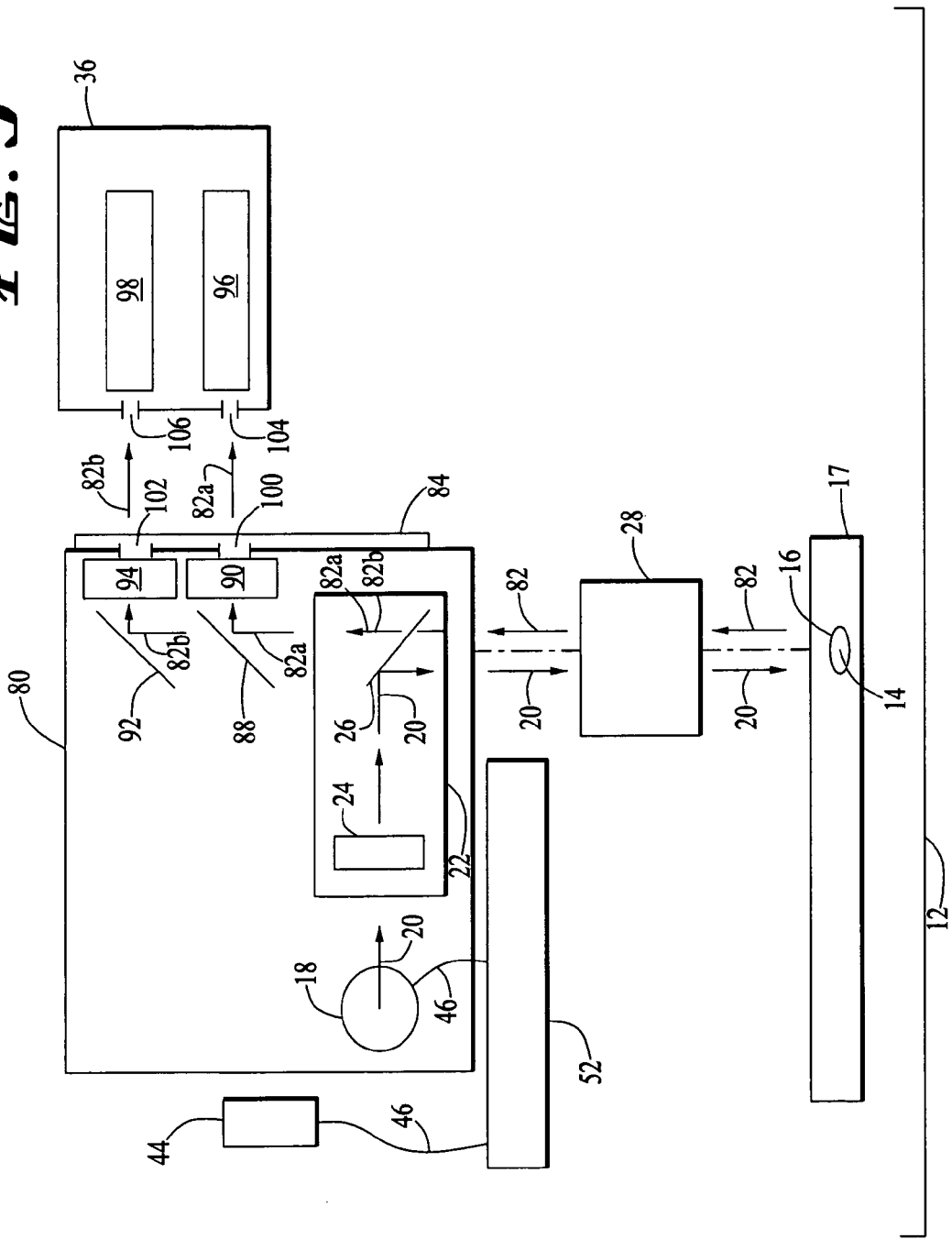

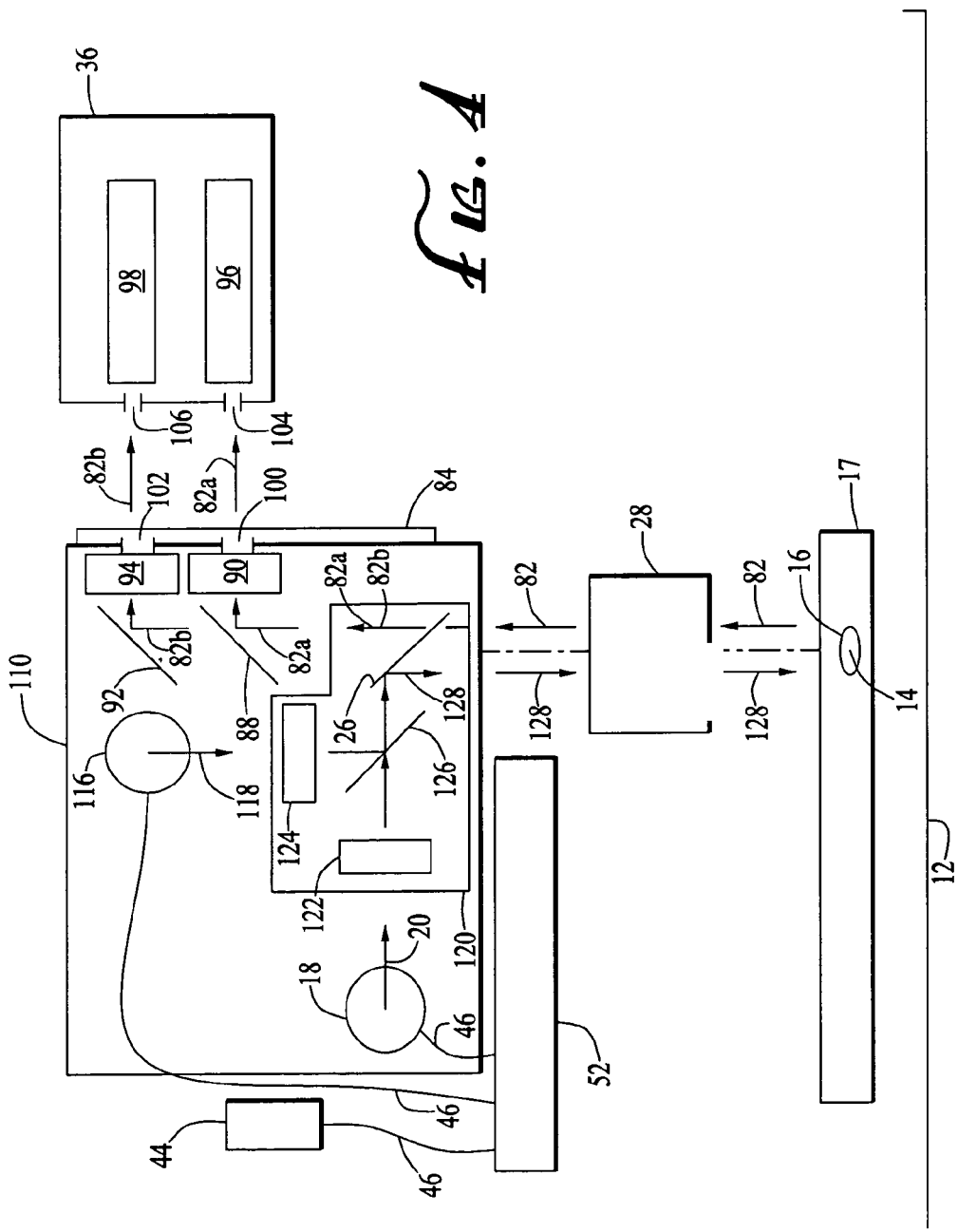
Fig. A

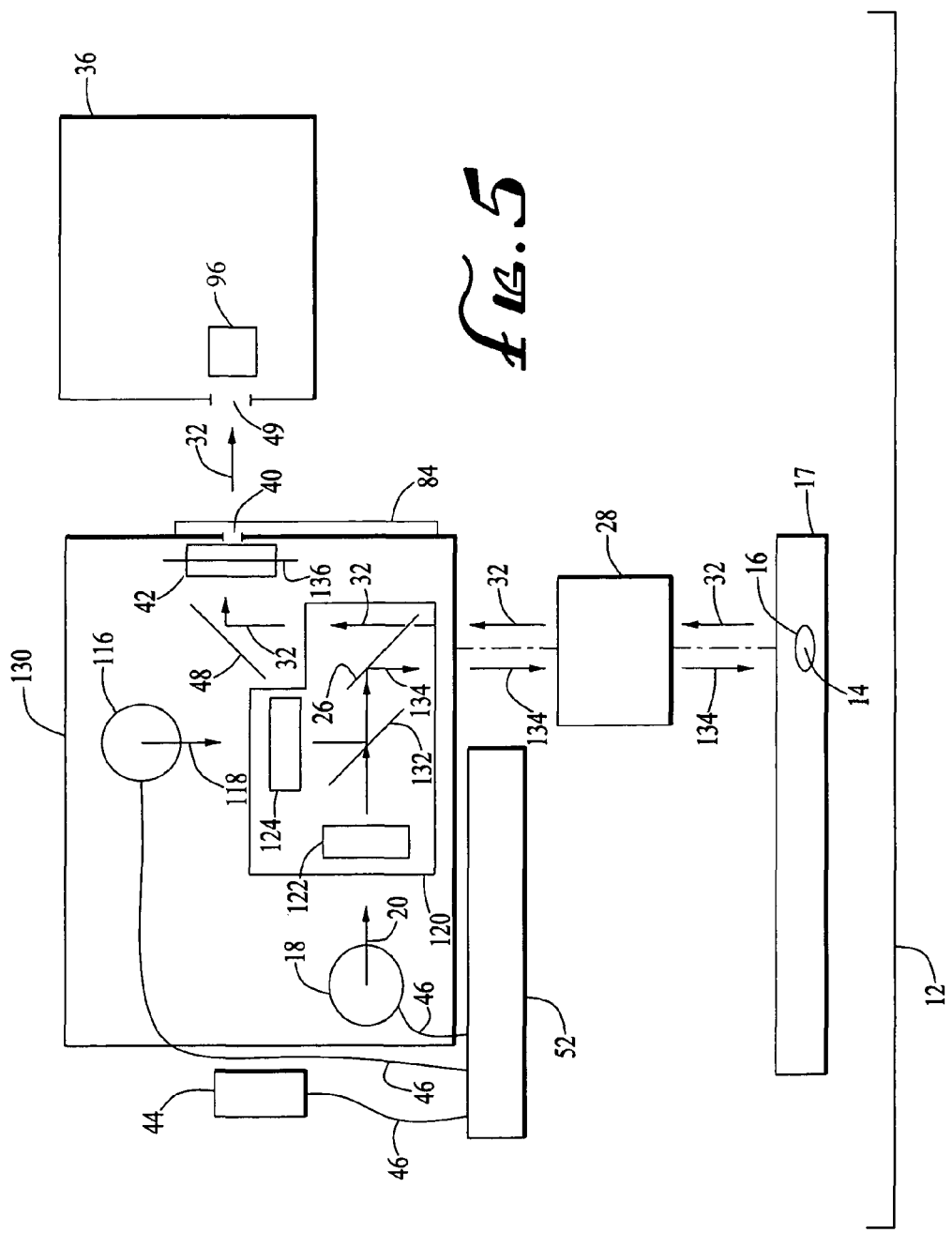

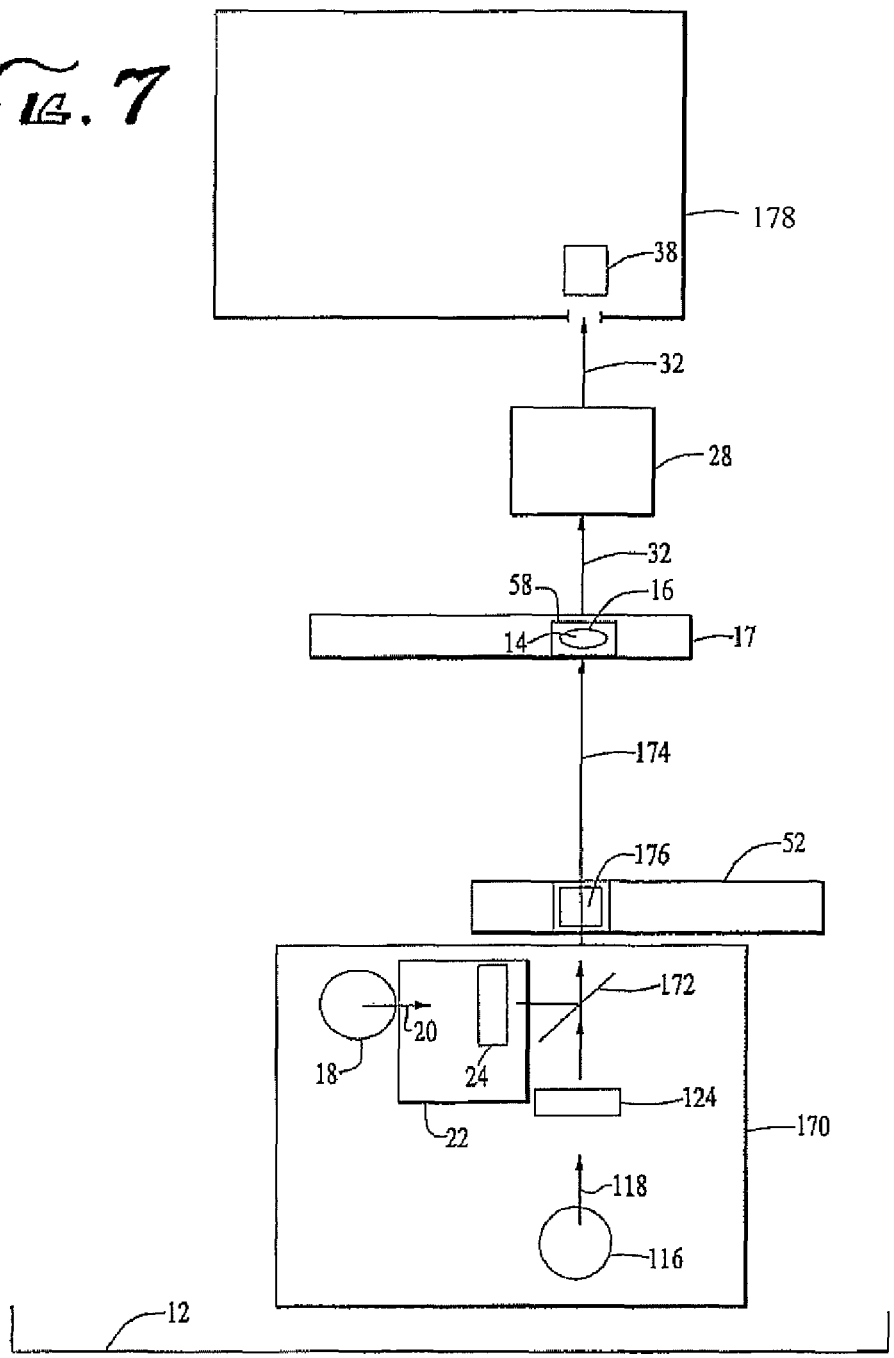

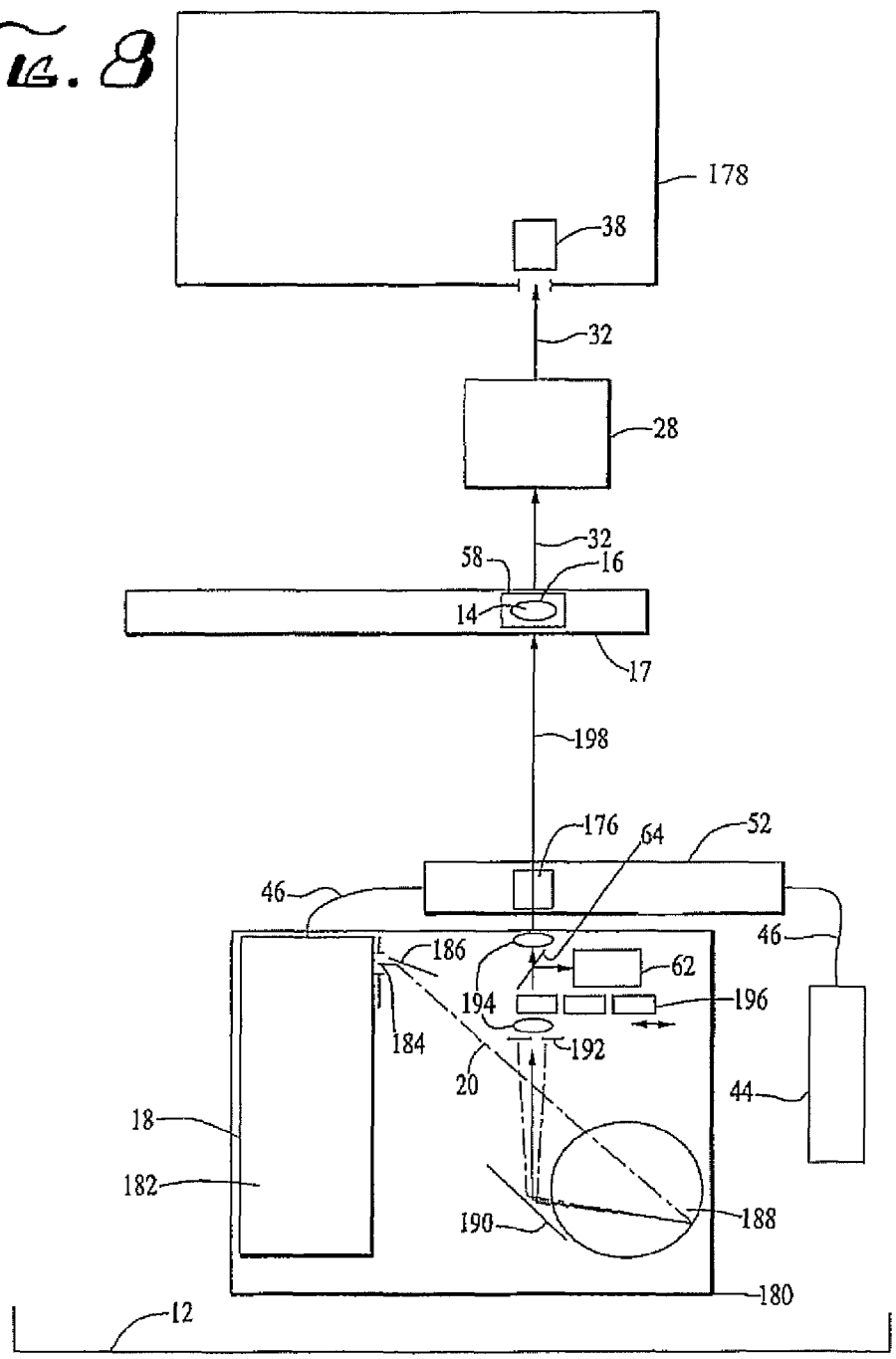

MULTIMODE READER

BACKGROUND

Multimode analytical instruments, also referred to as multimode readers, are apparatus that can perform multiple analytical assays in a single instrument. Standard multimode readers, used within the life science industry, can measure the most common types of assays (i.e., applications, such as fluorescence, luminescence, and absorbance) in a single instrument. The use of a single instrument to perform these assays is advantageous over using multiple dedicated instruments to perform the same measurements. This lies in the fact that a multimode reader can provide ease of use, a better price performance ratio, and require less bench top area than multiple instruments.

Multimode readers having a certain level of modularity are known. Further information on these instruments can be found in US Patent Application Nos. 2005/0012929; 2005/0105080: and US 2003/0048447, for example.

Generally, these instruments have built-in general purpose (i.e., white) light sources, such as halogen lamps and xenon flash lamps, and general purpose detectors such as photomultiplier tubes (PMTs) and silicon photodiodes. Also, in these instruments, optical filters have been mounted into wheels or slides, and application specific beamsplitters have been installed into slides, or into revolver like mechanisms.

However, with the above described instrumentation, performing a specific application means, from the hardware point of view, accessing a multitude of driven stages, at runtime, for selecting the correct combination and adjustment of filters, beamsplitters, apertures, and lightguides, for example. In these devices, enabling new applications of a given technology requires retrofitting specific optical filters and beamsplitters. Further, new configurations demand the correct definition for the new filters within the instrument control software.

Therefore, there is a need for an improved and more efficient multimode reader instrument. There is also a need for a multimode reader instrument that can change applications and have the identification of the programmed parameters for the new application be performed automatically. Finally, there is a need for a multimode reader instrument that can be easily upgraded for new types of applications.

SUMMARY

The present invention is a next generation design for multimode readers that satisfy these needs. The multimode reader apparatus incorporates a removable cartridge system in a "plug-in" format. The removable "plug-in" cartridges house the light sources, optics, and components that are specific for a selected optical application, such as fluorescence, absorbance, or luminescence. The cartridges can be seen as instruments within an instrument. The "plug-in" cartridge format allows the apparatus to be configured, customized, and upgraded by the user and is also easily serviceable. Further, the cartridge system allows for upgrades and use of the latest advancements in technology, like high power LED light sources. Since the cartridges are installable in an apparatus by a non-technical user, this not only eases retrofit of new applications, but the system may also accommodate applications based on technologies not yet existing today, at least as far as the corresponding components, such as the power supply, total power consumption, and the heat removal are already designed into the original apparatus.

According to the present invention, a cartridge for use in an apparatus for analyzing a target in a sample is provided. The apparatus has a power source, and the target is capable of generating an emitting light in response to an exciting light. The cartridge is adapted to be removably engaged with the apparatus and comprises a light source for producing an exciting light, a coupler for providing power to the light source from the power source, and a first optical system for directing the exciting light to the target. The first optical system comprises at least one component selected from the group consisting of apertures, photodiodes, optical filters, beam splitters, and light guides.

The apparatus also has a detector, and may also have a second optical system for receiving emitting light from the target and directing the emitting light from the target to the detector. This embodiment is used for applications directed to fluorescence detection. The cartridge may be a dual emission cartridge having a dual channel detector. According to this embodiment, the second optical system comprises a beam splitter which receives emitting light from the target and splits the emitting light into dual emitting lights, which are directed to the dual channel detector.

Preferably, for fluorescence applications, the light source is an LED light source, and the cartridge may have an electronic current supply that is capable of pulsing the LED light source, and a control for changing the intensity of the exciting light from the LED light source, and/or a photodiode that is capable of measuring the intensity of exciting light produced by the light source, which may be used to stabilize the LED light source. In other applications, such as for absorbance measurement, the light source may be a Xenon flash lamp module, the module having a Xenon flash lamp as the light source and having the corresponding electronics to produce a pulsed light source. In the case of using a wide band light source, such as a Xenon flash lamp, the optical system includes a wavelength selector for controlling the wavelength of the exciting light.

In a preferred, but not required embodiment, for fluorescence applications, the combination of the exciting light and the optical system in the cartridge produces a radiant light, a portion of which is capable of being absorbed by the target and causing the target to generate the emitting light, which is a fluorescent light. In another preferred, but not required embodiment, for absorbance applications, the combination of the exciting light and the optical system produces a radiant light, a portion of which is capable of being transmitted through the target to generate the emitting light which is attenuated in intensity.

In another embodiment according to the present invention, a multiple (e.g., dual) excitation cartridge for use in an apparatus for analyzing a target in a sample is provided. According to this embodiment, the apparatus has a power source, and the target is capable of generating an emitting light in response to an exciting light. The multiple excitation cartridge is adapted to be removably engaged with the apparatus and comprises a first light source for producing a first exciting light, a second light source for producing a second exciting light, a coupler for providing power to the first and second light sources from the power source; and a first optical system for directing one or both of the exciting lights to the target. In certain embodiments, both the first light source and the second light source contribute to the exciting light that is directed to the read head, and in other embodiments, the cartridge has a selector for selecting between the first light source and the second light source.

In a preferred but not required embodiment, such as for fluorescence applications, the apparatus has a detector, and the cartridge has a second optical system for receiving emitting light from the target and directing the emitting light from the target to the detector. In certain embodiments, the wavelengths of the first exciting light and the second exciting light, respectively, are different, and in other embodiments, the wavelengths of the first exciting light and the second exciting light, respectively, are substantially the same, but differ in polarization. In another embodiment, the cartridge also has a third optical system that receives emitting light from the target and directs the emitting light from the target to the detector.

In another embodiment, the dual excitation cartridge may also have a movable support, such as a revolving support, for supporting the first and second light sources and the second and third optical systems and moving the first and second light sources into a selected position for directing the exciting lights to the sample. According to this embodiment, the movable support may house multiple light sources, such as 3, 4, 5, or 6, and their corresponding optical systems.

According to another embodiment of the present invention, a luminescence cartridge for use in an apparatus for analyzing a target in a sample is provided. The apparatus has a read head and a detector, and the target is capable of generating an emitting light. According to this embodiment, the cartridge is adapted to be removably engaged with the apparatus and comprises an integrated read head and a driver for moving the integrated read head and an optical system for receiving emitting light from the target and directing the emitting light from the target to a detector. Preferably, the integrated read head is a rigid lightguide and the lightguide is capable of being moved toward the sample from within the cartridge.

According to another embodiment of the present invention, a cartridge system for use in an apparatus for analyzing a target in a sample is provided. According to this embodiment, the apparatus has a detector and a read head, and the target is capable of generating an emitting light in response to an exciting light. The cartridge system comprises a plurality of removable cartridges, at least one removable cartridge having a light source that produces an exciting light and a first optical system for directing the exciting light to the target, and a support configured to receive the plurality of cartridges and align each removable cartridge with the detector and read head. Preferably, the cartridge having a light source that produces the exciting light also has a second optical system that directs the emitting light from the target to the detector.

According to another embodiment of the present invention, a cartridge system mounted on a movable support, for use in an apparatus for analyzing a target in a sample is provided.

According to this embodiment, the cartridge system comprises a structure having a first support, a power source attached to the structure, a detector attached to the structure, and a first cartridge removably engaged with the first support. The first cartridge contains (i) a first light source for producing a first exciting light, (ii) a coupler for providing power to the first light source from the power source; and (iii) a first optical system for directing the first exciting light to the target. The cartridge system also has a read head containing a second optical system that cooperates with the first cartridge for directing the first exciting light to the target. According to a preferred embodiment, the read head cooperates with the first cartridge for directing the emitting light from the sample to the first cartridge, and the first cartridge also has a third optical system for receiving emitting light from the read head and directing the emitting light from the read head to the detector. In certain embodiments, the detector is a dual channel light detector.

The system may also have an injecting cartridge for injecting a reagent into the sample in the first cartridge, where the injecting cartridge may have a reagent reservoir, a pump, and a movable nozzle that is movable toward the sample in the first cartridge from within the injecting cartridge.

In other embodiments, the system may also have a sample support and a sample support detector for clearance of the sample support which comprises a light source, a reflector and a light source detector.

The system may also have multiple other removable cartridges, such as those described herein, which are removably engaged with the first support in a concurrent fashion, and selectively align each removable cartridge with the read head and the detector. Preferably, each of the multiple cartridges may be removed from the first support and exchanged on the first support with another cartridge. More preferably, the cartridges may be removed and exchanged without the use of mechanical tools, or with a simple mechanical tool to remove a clip mechanism.

Preferably, the cartridges contained in the system have an indicia indicating the type of detection the cartridge can be used for, and the apparatus further comprises a cartridge detector for detecting the indicia, which may be positioned on the first support, and the indicia is an electrically erasable programmable read-only memory.

In an alternate embodiment, the system has multiple cartridges, such as those described herein, but the system additionally has a second support and one or more of the cartridges is removably engaged with the second support. According to this embodiment, the system may also have a dual light guide for directing emitting light from the cartridge contained on the second support to a detector. The system may also have a sample carrier which is positioned between the first support, and the second support.

According to this embodiment, the system may also have a detector port having a switch that is switchable between different lights produced from the multiple cartridges and may also have a shutter which is moveable to a position in front of the detector port, and/or one or more attenuating filters that are moveable to a position in front of the detector port.

According to another embodiment, a cartridge system for reagent injection for analyzing a target in a sample is provided, the target being capable of generating an emitting light. According to this embodiment, the system comprises a structure having a first support and a second support; a power source attached to the structure, and a detector attached to the structure. The system also has a first cartridge removably engaged with the first support, the first cartridge having a reagent reservoir, a pump, and a movable nozzle for injecting a reagent into the sample, and a second cartridge removably engaged with the second support, the second cartridge having a first optical system for directing the emitting light from the target to the detector. A read head containing a second optical system that cooperates with the first cartridge directs the emitting light to the detector.

According to another embodiment, a method for fluorescence measurement using photoactivation of a functional group associated with a target in a sample is also provided. The functional group is capable of changing from an inactivated state to an activated state in response to a first exciting light and is capable of producing an emitting light in response to a second exciting light. According to this method, first, a cartridge having a first exciting light source and second exciting light source, the first and second light sources being capable of producing first and second exciting lights, respectively, is selected. The cartridge also has a first optical system for directing the first and second exciting lights to the sample and a second optical system for directing the emitting light to the detector. Then, the first exciting light is directed to the functional group associated with the target in the sample, which changes the functional group associated with the target from an inactivated state to an activated state. The second exciting light is then directed to the functional group associated with the target in the sample, which produces an emitting light from the functional group associated with the target. The emitting light is then directed to a detector, preferably, via a read head and the second optical system within in the cartridge. A signal that corresponds to the emitting light detected by the detector is then produced, and also, a read-out of the signal may be produced.

According to another embodiment, a method for analyzing a target in a sample is also provided. The method comprises selecting a cartridge system having first and second cartridges, such as one of the systems described herein and replacing the first cartridge with the second cartridge. Then, a target in a sample is analyzed with the second cartridge. Replacing the cartridge preferably comprises removing the first cartridge from the apparatus and substituting the first cartridge with the second cartridge in the apparatus without the use of mechanical tools. After replacement, the system is instructed, with apparatus-readable instructions, with information for analyzing the sample.

In another embodiment, a method for analyzing first and second targets in first and second samples with multiple cartridges is provided.

BRIEF DESCRIPTION OF THE FIGURES

These and other features, aspects and advantages of the present invention will become better understood from the following description, appended claims, and accompanying figures where:

FIG. 2 is a schematic illustration of a cartridge having source intensity monitoring components according to an embodiment of the present invention;

FIG. 3 is a schematic illustration of a dual emission cartridge according to an embodiment of the present invention;

FIG. 4 is a schematic illustration of a dual emission dual excitation cartridge according to an embodiment of the present invention;

FIG. 5 is a schematic illustration of a dual excitation cartridge according to an embodiment of the present invention;

FIG. 7 is a schematic illustration of a dual wavelength absorbance cartridge according to an embodiment of the present invention;

FIG. 8 is a schematic illustration of a wide band light source cartridge with wavelength selection according to an embodiment of the present invention;

DETAILED DESCRIPTION

According to the present invention, a cartridge for use in an apparatus for analyzing a sample is provided. The cartridge has one or more light sources, as well as optical systems and other components, which are specific for a certain type of application such as fluorescence or absorbance. The light source, optical systems, and other components for a specific application are housed in a single cartridge. The cartridge is removably engaged with the apparatus in a "plug-in" format such that the apparatus can be upgraded by substitution or installation of a cartridge, i.e., a new application can be installed by adding or substituting a new cartridge in the apparatus, or an installed cartridge can be substituted with another cartridge of the same purpose which incorporates the latest advancements in technology. The new cartridge may have its components preadjusted and pretested and the cartridge may be automatically identifiable by the apparatus such that the instrument control software can identify an individual cartridge and recognize any application specific parameters stored in the cartridge. Thus, instead of selecting a combination of light sources, optics, and other components for a new application, running a new application is reduced to selecting a single component, i.e., the cartridge, with its interior components preadjusted and pretested, and installing the cartridge in the apparatus. An advantage of the cartridge concept is that an instrument can be upgraded in the field by the user himself—without needing the assistance of a service engineer.

The apparatus may have general purpose detectors (like photomultipliers and photodiodes), which are shared by multiple cartridges, and all applications of the same technology may share certain read heads that interface with the samples to be measured.

Figure 1A:
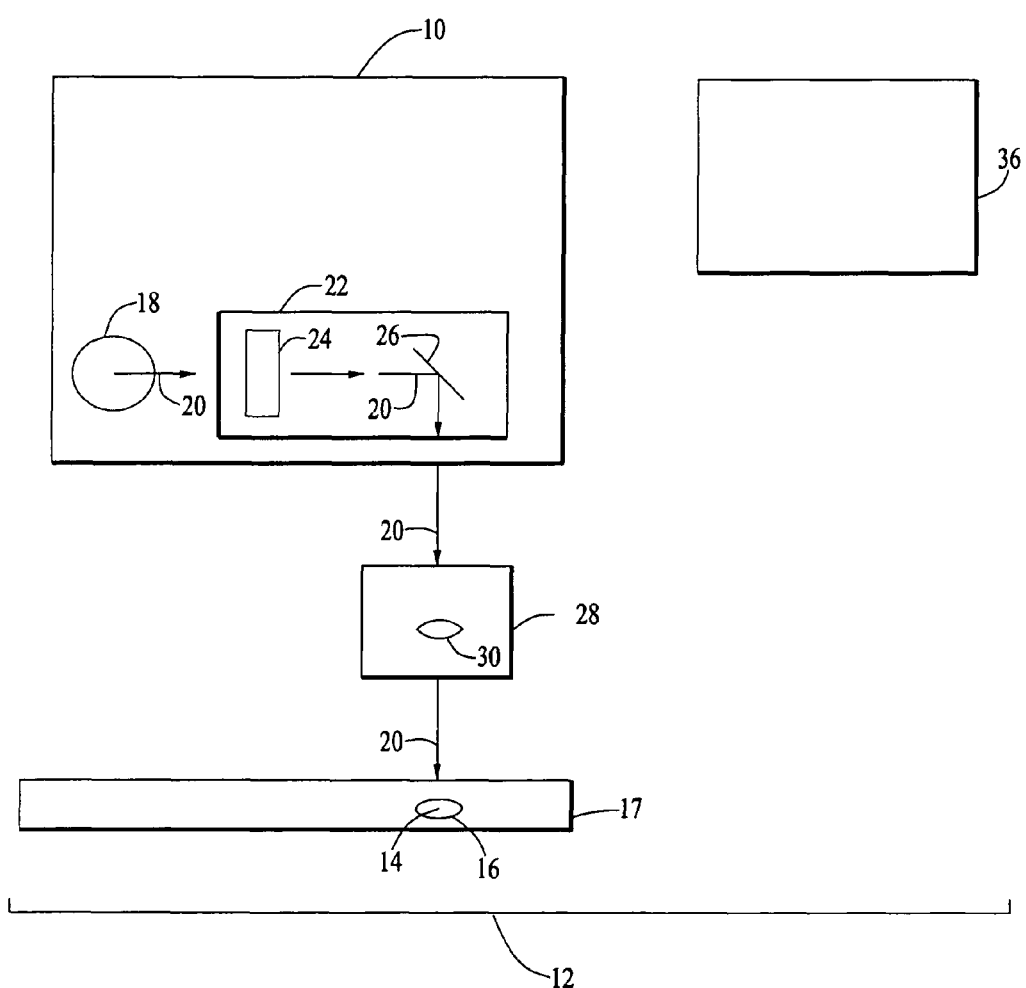
FIG. 1A is a schematic illustration of the components of a cartridge according to an embodiment of the present invention.
Figure 1B:
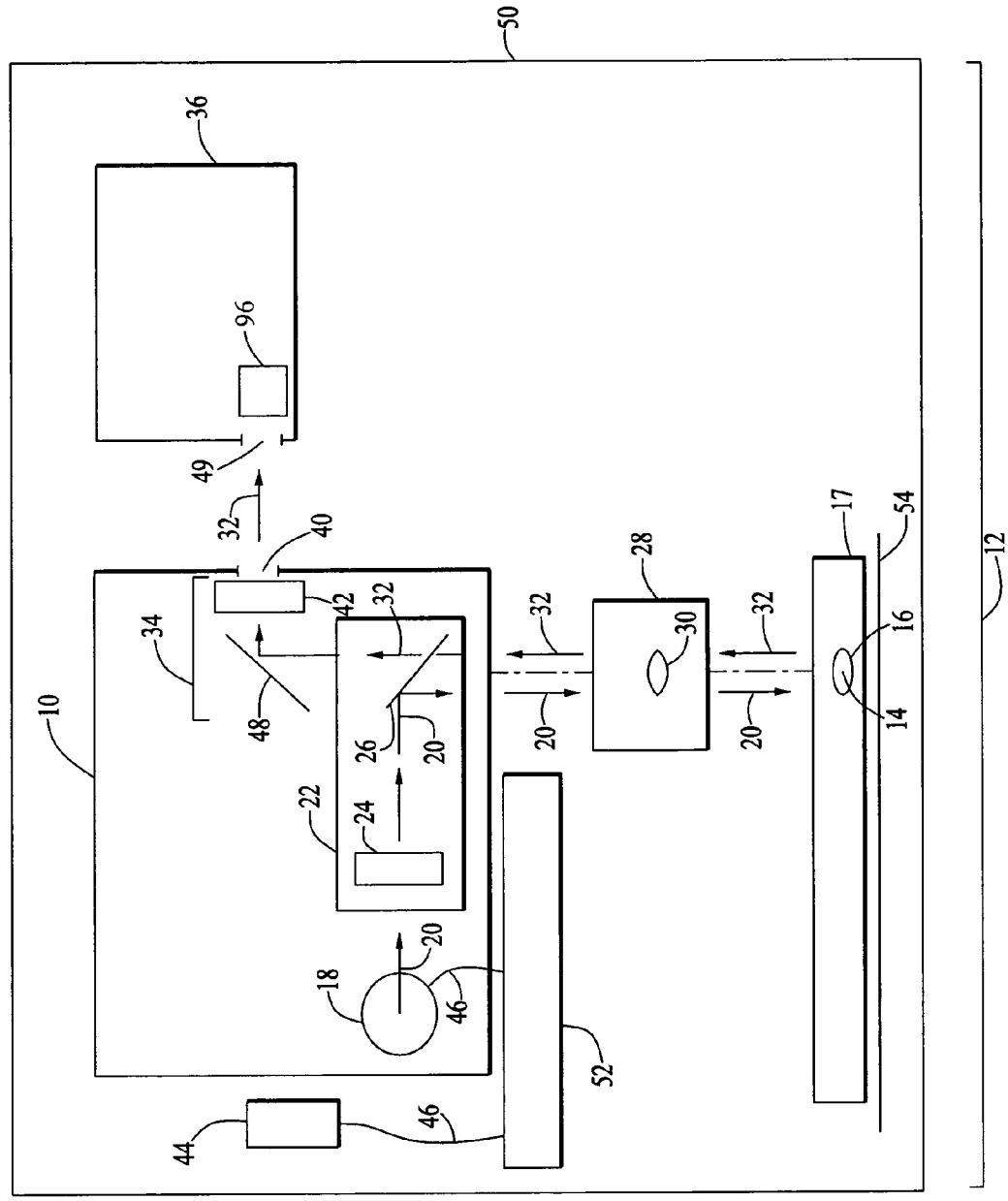
FIG. 1B is a schematic illustration of the components of a cartridge used for a fluorescence application according to an embodiment of the present invention.
Figure 1C:
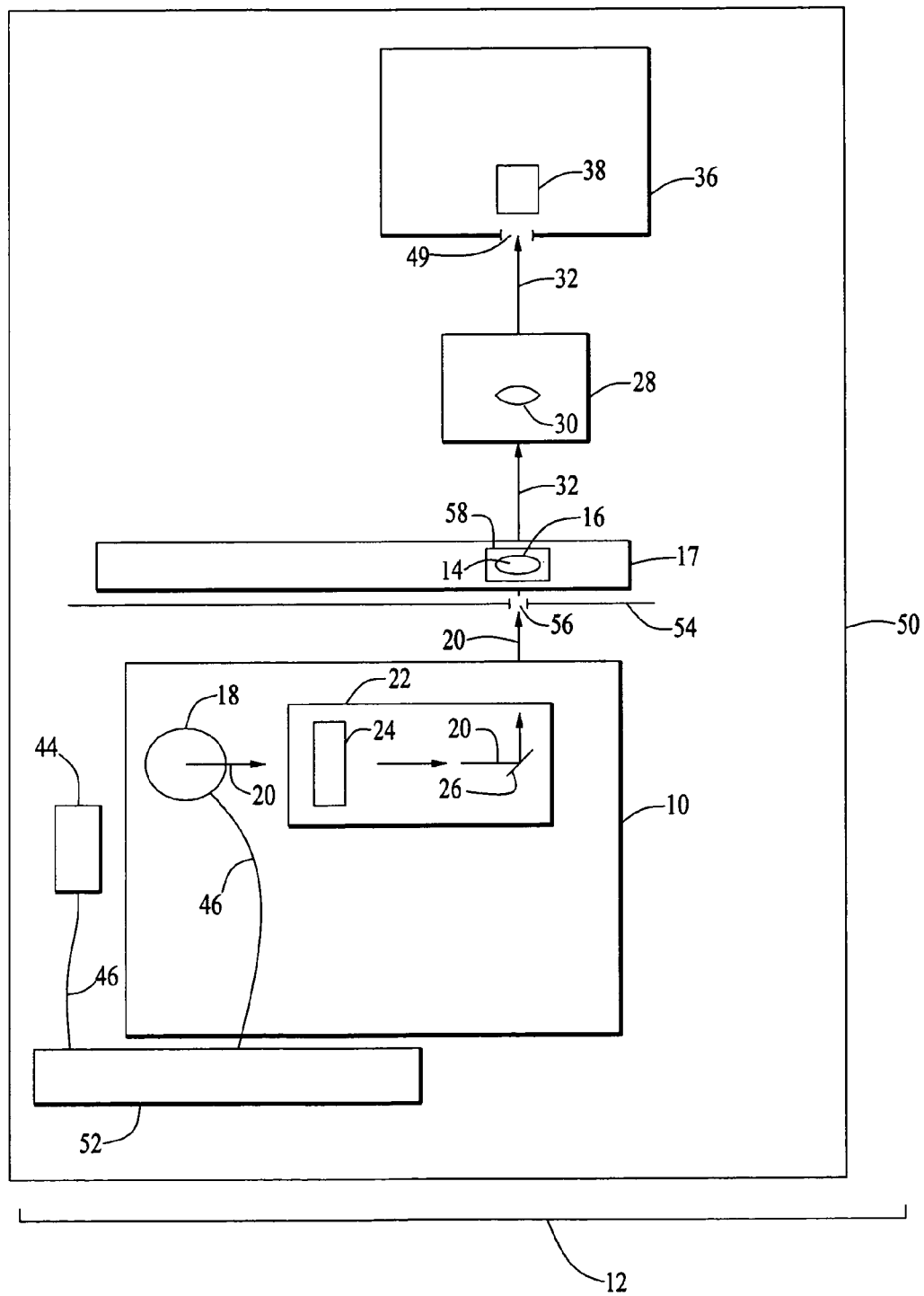
FIG. 1C is a schematic illustration of the components of a cartridge used for an absorbance application according to an embodiment of the present invention.

Referring now to FIGS. 1A, 1B, and 1C a cartridge 10 for use in an apparatus 12 for analyzing a target 14 in a sample 16 is shown. The sample 16 may be held within the apparatus 12 on a sample support 17, such as a microplate. As shown in FIG. 1, the cartridge 10 comprises one or more light sources 18 that separately or in combination produce an exciting light 20. The cartridge 10 is designed to be removably engaged with the apparatus 12. The cartridge 10 has a first optical system 22 which has components for directing the exciting light 20 to the sample 16. The light source 18, such as an LED or a Laser Diode, is collimated by lenses and apertures to emit a collimated beam of light. The first optical system 22 then transmits the exciting light 20 through filters 24, such as a bandpass filter, and then reflects the exciting light 20 out of the cartridge 10 with the help of a reflector 26, such as a dichroic beamsplitter, to a read head 28. The read head 28 directs the exciting light 20 toward the sample 16. The read head 28 contains an objective lens 30 that can be moved up and down. The objective lens 30 focuses the exciting light 20 onto the sample 16. The sample 16, containing the target 14, then produces an emitting light 32, which is directed to a detector 36, having a photomultiplier tube (PMT) 96, as shown in FIG. 1B, or a photodiode 38, as shown in FIG. 1C.

As also shown in FIGS. 1B and 1C the apparatus 12 is part of a system for analyzing a sample. The system comprises a structure 50, also referred to herein as a housing, which is engaged (i.e., attached) to the read head 28, the detector 36, a power source 44, and a movable cartridge support 52. The movable cartridge support 52 positions the cartridge 10 within the apparatus 12 and is capable of supporting a plurality of cartridges and aligning each cartridge with the read head 28 and the detector 36. The cartridge 10 has a coupler 46 for providing a current supply from the power source 44 to the light source 18. Preferably, the cartridge 10 is mounted onto the support 52 and a plug terminating the electronics inside of the cartridge 10 is connected with a socket in the support 52. At the socket, several low voltage output lines of the power source 44 are available and interface lines with the main apparatus controller. The coupler 46 functions in connecting the cartridge 10 with other components in the apparatus 12, such as for receiving low DC voltage for the cartridge light source 18 and other electronics; establishing control lines for LED current adjustment; establishing control lines for cartridge recognition; data lines (e.g., an electronic bus) for detectors within the cartridge 10 (e.g., a photodiode for sending measured data to a controller); and synchronization lines for synchronizing pulses of the light source 18 with the data acquisition from detector(s) and other circuitry within the apparatus 12, such as photon counting circuitry in the main apparatus controller. Preferably, the coupler 46 is made from two parts, a printed circuit board that extends along the cartridge support 52, providing a socket for one or more cartridges 10, and a flexible flat cable at the end, bridging the gap to the main apparatus controller (flexible, because the cartridge support 52 can be moved). The electronic bus, or data line function is designed as of the type SPI (serial peripheral interface).

The system may also have a sample support carrier 54, such as a microplate scanning stage, attached to the structure for moving the sample support 17 either horizontally or vertically within the housing (e.g., structure 50).

Referring now to FIG. 1B, in certain embodiments, such as a cartridge 10 that is used for a fluorescence application, the emitting light 32 is collected from the target 14 by the read head 28 and collimated back into the cartridge 10. The cartridge 10 has a second optical system 34, which receives the emitted light 32 from the read head 28 and directs the emitted light 32 from the sample 16 to the detector 36. The emitting light 32 received from the read head 28 is transmitted through the reflector 26, and is then directed with a reflector 48 towards the cartridge exit 40, which interfaces with the detector 36 via a detector port 49. Before exiting the cartridge 10, the emitted light 32 is filtered through a filter 42, such as a bandpass filter, to reject contributions of excitation light being scattered back from the read head 28 and the sample 16. The entire path after the emitted light 32 has passed through the reflector 26 is optically shielded from those areas of the cartridge 10 which may be floated with diffuse scatter of exciting light 20.

Referring now to FIG. 1C, in certain embodiments, a cartridge 10, such as a cartridge that is used for an absorbance application, is positioned in the apparatus 12 in opposite to the detector 36. According to this embodiment, the exciting light 20 is transmitted through the sample 16 and sample support carrier 54 via an aperture 56 (i.e., a window or light transparent portion) in the sample support carrier 54 and an aperture 58 (i.e., a window or light transparent portion) in the sample support 17. Emitting light 32 from the target 14 is directed to the detector 36 (containing, e.g., a photodiode 38). The configuration of the cartridge 10 for measuring absorbance as shown in FIG. 1C is shown by way of example and other configurations are possible, for example, the cartridge 10 may be alternately positioned within the apparatus 12, such as in the same approximate plane as the detector 36 (e.g., side-by-side), and the emitting light 32 may be relayed to the detector 36, such as with a light guide, as will be understood by those of skill in the art with reference to this disclosure.

The one or more light sources 18 housed in the cartridge 10 may be selected from suitable light sources known to those of skill in the art such as light emitting diodes (LEDs), laser-diodes, and a Xenon flash lamp module. Preferably, when the cartridge 10 is used for a fluorescence application, such as shown in FIG. 1B, the light source 18 is one or more LED light sources. Preferred LED light sources are obtained from Lumileds, San Jose, Calif., US (for various peak wavelengths between 350 nm and 700 nm; Luxeon Star, Nichia, Tokushima, Japan, for various peak wavelengths between 350 nm and 700 nm; and Roithner-Laser, Vienna, Austria, for various peak wavelengths between 350 nm and 700 nm. Preferably, when the cartridge 10 is used for an absorbance application, such as shown in FIG. 1C, the light source 18 is a Xenon flash lamp module. Preferred Xenon flash lamp modules are obtained from Perkin Elmer Optoelectronics, Fremont, Calif., US, product name RSL3100; and Hamamatsu Photonics, Japan, product name L9455.

Referring now to FIG. 2, another embodiment of the apparatus 12 for analyzing a target 14 in a sample 16 is shown. According to this embodiment, the apparatus 12 has a source intensity monitoring cartridge 60 with a light source 18 and a first optical system 22 which has components for directing an exciting light beam 20 to a sample 16 via a read head, as described with respect to FIG. 1B. The cartridge 60 is designed to be removably engaged with apparatus 12 via the movable cartridge support 52. In certain embodiments, the cartridge 60 has a second optical system 34 (not shown), as described with respect to FIG. 1B, which receives emitting light 32 from the sample 16 via the read head (not shown) and directs the emitting light 32 from the sample 16 to the detector 36.

According to the embodiment shown in FIG. 2, during or prior to signal detection at the detector 36, the exciting light beam 20 is passed through an excitation filter 24 and a portion of the exciting light beam 20 is reflected onto a light source detector 62 (e.g., a photodiode) with a partially reflecting mirror 64 as reflected light 66. Electronic circuitry 68 measures the intensity level of the reflected light 66. The measured intensity level of the reflected light 66 is used to stabilize the output of the light source 18 via a feedback loop 70.

In another embodiment shown in FIG. 2, when analyzing a target 14 in a sample 16 with the detector 36 using a fluorescence method, as described with respect to FIG. 1B, the electronic path 72a, 72b, and 72c may be applied to extend the generic dynamic range of the detector 36. According to this embodiment, the light source 18 is first adjusted to a maximum intensity, and the intensity of the emitting light 32 is tested (for quite a short pre read time to give a pre read value) at the detector 36. The main controller 74 receives the tested emitting light signal from the detector 36 via path 72c and may adjust the intensity of the exciting light 20 (i.e., the source intensity) by addressing the controller 68 via control line 72a and 72b. Preferably, when detecting a superthreshold signal at detector 36, the main controller 74 reduces the intensity of the exciting light 20 by adjusting the power to light source 18 according to the pre read value. In this preferred embodiment, the target 14 is measured with a longer read time, as selected by the user, and the intensity of the signal from the emitting light 32 found at the detector 36 is normalized with the actual value of the intensity of the exciting light 20, because the intensity of the emitting light 32 changes according to the intensity of the exciting light 20. Thus, the read out becomes comparable with measurement values taken at other light source intensity levels.

In fluorescence applications, the LED light source(s) are typically supplied with constant current for reading of prompt fluorescence, where prompt fluorescence is differentiated from time delayed fluorescence reading, e.g., in prompt fluorescence, the fluorescence emission is instantaneously gone when the light source is switched off—unless operating on nanosecond time scales (fluorescence labels having typical decay times of about 1 to about 10 nanoseconds). In other fluorescence applications using a light source 18 that can be pulsed (e.g., LEDs, Laserdiodes, and Xenon flash lamps), enables the measurement of fluorescence with a time delay (i.e., "time-resolved", in connection with lanthanide ion labels having decay times between about 20 and about 2,000 microseconds). In such applications, the photon counting electronics, (to be thought as included in the detector 36) monitoring the sample emission are enabled (gated by the controller 74 via control line 72c) with a short time delay after the light source 18 has been switched off by controller 74 via control line 72a and 72b.

Referring now to FIG. 3, another embodiment of the apparatus 12 for analyzing a target 14 in a sample 16 is shown. According to the embodiment shown in FIG. 3, the apparatus 12 has a dual emission cartridge 80 that is capable of measuring dual label assays. The dual emission cartridge 80 is designed to be removably engaged with apparatus 12 via the movable cartridge support 52. Certain assays profit from measuring two different emission wavelengths at the same time (e.g., Fluorescence Resonance Energy Transfer (FRET) type assays), and measuring two different emission wavelengths at substantially the same time can result in a total time saving for the user due to the reduced read time.

According to the embodiment shown in FIG. 3, the apparatus 12 has a light source 18 which produces an exciting light 20, such as described with respect to FIG. 1B. The apparatus 12 additionally has a power source 44 and the cartridge 80 has a coupler 46 for providing a current supply to the light source 18 from the power source 44. The dual emission cartridge 80 has a first optical system 22 which has components, including an excitation filter 24, for directing the exciting light 20 to a sample 16 via a read head 28. The read head 28 directs the exciting light 20 toward the sample 16. The sample 16, containing the target 14, produces an emitting light 82. The dual emission cartridge 80 has a second optical system 84, which receives the emitting light 82 from the read head 28 and directs the emitting light 82 from the sample 16 to a detector 36. The emitting light 82 contains two wavelength bands 82a and 82b which are both passed through the reflector 26. The first wavelength band 82a is reflected by a beamsplitter 88 toward the detector 36 via a first emission filter 90 (e.g., a bandpass filter). The second wavelength band 82b is passed by the beamsplitter 88, and reflected at a mirror 92 toward the detector 36 via a second emission filter 94 (e.g., a bandpass filter). The detector 36 is a dual channel detector which preferably has two detectors 96 and 98, preferably photomultiplier tubes which are stacked to form the dual channel detector. In addition, the cartridge 80 has a dual exit port 100 and 102, which is aligned with the detectors 96 and 98 via detector ports 104 and 106. The detector ports 104 and 106 may include collecting lenses that focus the quasi collimated emission light onto the active area(s) of the detector 36, which is typically smaller than the emission light 82 beam diameter.

Referring now to FIG. 4, another embodiment of the apparatus 12 for analyzing a target 14 in a sample 16 is shown. According to the embodiment shown in FIG. 4, the apparatus 12 has a dual emission dual excitation cartridge 110 that is equipped with a second light source 116. The cartridge 110 is designed to be removably engaged with apparatus 12 via the movable cartridge support 52. When light sources which can be pulsed are used, such as LEDs or laserdiodes, the first and second light sources 18 and 116 may be electronically switched, and different wavelengths of light may be used to measure a sample. According to this embodiment, there is no need to mechanically switch between different wavelengths of light, which results in a saving of total measurement time.

According to the embodiment shown in FIG. 4, the apparatus 12 has a first light source 18 which produces a first exciting light 20 and a second light source 116 which produces a second exciting light 118. The apparatus 12 additionally has a power source 44 and the cartridge 110 has a coupler 46 for providing a current supply to light sources 18 and 116 from the power source 44. The dual emission dual excitation cartridge 110 has a first optical system 120 which has components, including a first excitation filter 122 and a second excitation filter 124, for directing the first and second exciting lights 20 and 118, respectively, to a beam combiner 126. The beam combiner 126 aligns the first and second exciting lights 20 and 118 to form a combined exciting light beam 128. The combined exciting light beam 128 is directed to the sample 16 via reflector 26 and read head 28. The sample 16, containing the target 14, produces an emitting light 82. The dual emission dual excitation cartridge 110 has a second optical system 84, as previously described with respect to FIG. 3, which receives the emitting light 82 from the read head 28 and directs the emitting light 82 from the sample 16 to detector 36.

In certain embodiments of the invention shown in FIG. 4, the dual emission dual excitation cartridge 110 is used to measure fluorescence polarization. According to this embodiment, the wavelengths of the first and second exciting lights 20 and 118 are essentially the same, and beam combiner 126 and beamsplitter 88 are polarizing cubes. The function of the second light source 116 is to determine the apparatus specific normalization factor for Fluorescence Polarization (G-Factor) by performing a calibration measurement.

Referring now to FIG. 5, another embodiment of the apparatus 12 for analyzing a target 14 in a sample 16 is shown. According to the embodiment shown in FIG. 5, the apparatus 12 has a dual excitation cartridge 130 that is equipped with a second light source 116. The cartridge 130 is designed to be removably engaged with apparatus 12. As described with respect to FIG. 4, when light sources that can be pulsed are used, the first and second light sources 18 and 116 may be electronically switched, and different wavelengths of light can be used to measure a sample. According to the embodiment of the cartridge 130 shown in FIG. 5, the second emission path (from FIG. 4) is omitted while the second excitation source is maintained. In a single emission configuration (preferable for matters of reducing costs), the dual excitation cartridge 130 enables the measurement of fluorescence polarization without mechanically moving polarization filters thereby saving valuable measurement time, as described in the following paragraph.

According to the embodiment shown in FIG. 5, the apparatus 12 has a first light source 18 which produces a first exciting light 20 and a second light source 116 which produces a second exciting light 118. The apparatus 12 additionally has a power source 44 and the cartridge 130 has a coupler 46 for providing a current supply to light sources 18 and 116 from the power source 44. The dual excitation cartridge 130 has a first optical system 120, as described with respect to FIG. 4, which has components, including a first excitation filter 122 and a second excitation filter 124, for directing the first and second exciting lights 20 and 118, respectively, to a polarizing beam splitter 132. The polarized light beam 134 is directed to a sample 16 via reflector 26 and read head 28. The read head 28 directs the exciting light 134 toward the sample 16. The dual excitation measurement may be performed quasi simultaneously, by alternating the polarization state of the beam, i.e., electronically switching between the first and second light sources 18 and 116. The sample 16, containing the target 14, produces an emitting light 32. The dual excitation cartridge 130 has a second optical system 34, as described with respect to FIG. 1B, which receives the emitted light 32 from the read head 28 and directs the emitted light 32 from the sample to the detector 36. The emitted light 32, received from the read head 28 is transmitted through a reflector 26 by a mirror 48 towards the cartridge exit 40, which interfaces with the detector 36. Before exiting the cartridge 130, the emitted light 32 is filtered through a filter 42 which is sandwiched with a polarization analyzing sheet 136. According to this embodiment, the G-Factor is determined using an assay standard.

According to another embodiment of the invention shown in FIG. 5, the dual excitation cartridge 130 may be used for a new type of microplate assay technology which uses two light sources in combination for photoactivation of a sample by one light source, followed preferably by a fluorescence measurement using the other light source. According to this embodiment, a first exciting light (e.g., exciting light 118 from light source 116) and a second exciting light (e.g., exciting light 20 from light source 18) are directed to the target 14 in succession, i.e., one after the other. The target 14 contains or is associated with a functional group having an inactivated state and an activated state, e.g. "caged" functional groups of biochemical starter reagents which are activated by flash photolysis. The first exciting light 118 is first directed to the target 14 to change the functional group associated with the target 14 from the inactivated state to the activated state (i.e., the functional group associated with the target 14 is photoactivated). The photoactivation of the functional group is followed by a fluorescence measurement which is accomplished by directing the second exciting light 20 to the target 14 associated with the functional group, which is in the activated state, to produce an emitting light 32 in response to the second exciting light 20. The second optical system 34 receives the emitting light 32 produced by the functional group on the target 14 and directs the emitting light 32 from the target 14 to the detector 36.

The above cartridge system used for photoactivation is described with respect to analyzing the target 14 in the sample 16 by a single emission fluorescence measurement. However, as will be understood by those of skill in the art by reference to this disclosure, the invention is not limited by the above described example, and other embodiments of the cartridge system employing a cartridge that is capable of photoactivating a target in a first step and reading an emission from the activated target in a second step are envisioned. For example, other fluorescence measurement configurations may be used according to the present invention, such as dual emission fluorescence (described with respect to FIG. 4, for example). Alternately, the target 14 in the sample 16 may be analyzed with other optical measurements such as absorbance or luminescence. For example, the target 14 in the sample 16 may be measured using absorbance. According to this embodiment, the cartridge has a dual light source, the first light source being used to activate the functional group on the target 14, as described with respect to FIG. 5, but the cartridge and apparatus are reconfigured for absorbance detection. In another example, the target 14 in the sample 16 may be measured using luminescence. According to this embodiment, the second light source in the cartridge is omitted and the first light source is used as an activating light source to activate the functional group on the target 14, as described with respect to FIG. 5, but the cartridge and apparatus are configured for luminescence detection.

The cartridge system used for photoactivation of a sample has several advantages over other analogous systems that employ reagent injection technology such as (i) photoactivation does not involve reagent injection, which imposes some risk of instrument contamination due to aerosol build up, splashes onto optics, and/or leakage; (ii) photoactivation does not require mixing of injected reagents, which can have incomplete mixing, and a lack of reproducibility; (iii) caged starter reagents may be brought right into living cells in order to trigger a reaction within a cell by external optical means. Such reactions cannot be triggered by the physical injection of starter reagents into the sample which contains such cells.

Figure 6A:
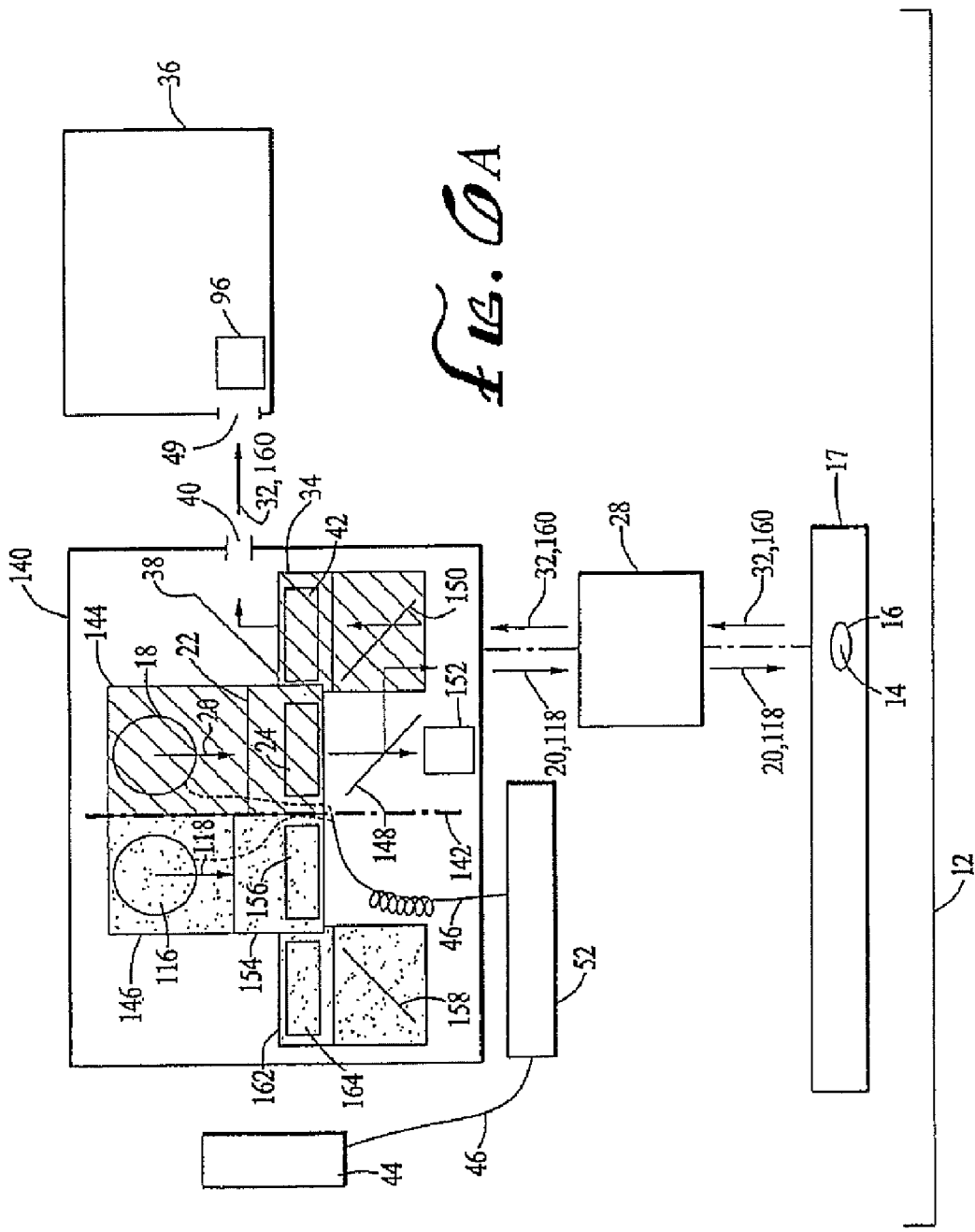
FIGS. 6A and 6B are a schematic illustration of a multi-purpose cartridge, having multiple applications mounted on a revolver mechanism within the cartridge, according to an embodiment of the present invention.
Figure 6B:
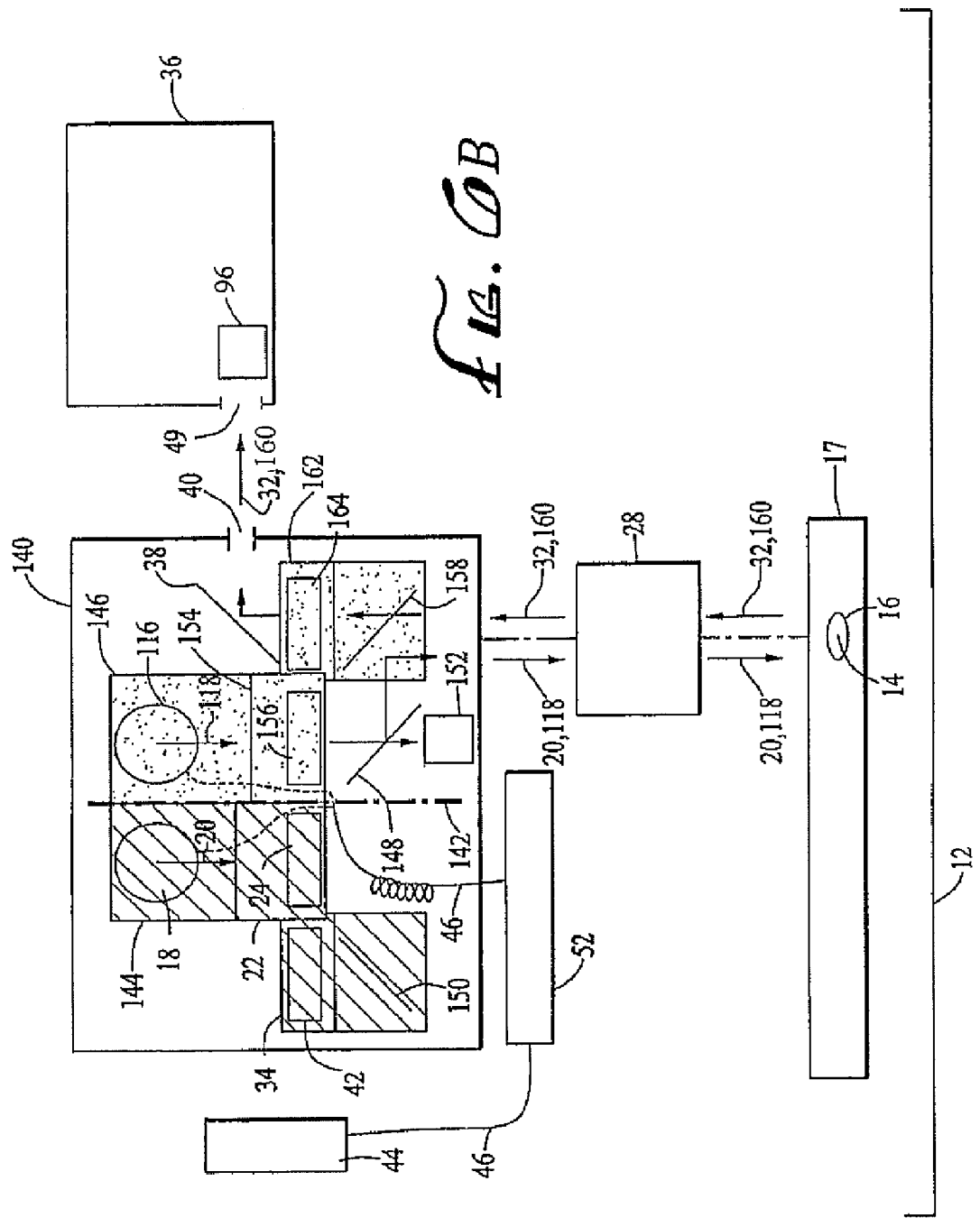

Referring now to FIG. 6A and FIG. 6B, another embodiment of the apparatus 12 for analyzing a target 14 in a sample 16 is shown. As shown in FIG. 6A and FIG. 6B, the apparatus 12 has a multi-purpose cartridge 140 that is equipped with multiple sections, or chambers, each section being configured for a particular spectroscopic application. The multi-purpose cartridge 140 may be equipped with multiple sections (e.g., 5 or 6), each chamber having an application specific set of light sources and/or optical systems that correspond to a particular application. In an alternative embodiment, a section (i.e., chamber, or section of the support) may be configured without a light source to provide a luminescence channel, i.e., luminescence light collected by the read head 28 is forwarded through a section of the cartridge 140 to the detector 36.

According to the embodiment shown in FIGS. 6A and 6B, the multi-purpose cartridge 140 has multiple light sources, each within a separate section, such as the first and second light sources 18 and 116, which are housed in first and second sections 144 and 146, respectively, as shown in FIGS. 6A and 6B. The multi-purpose cartridge 140 utilizes a revolver mechanism 142 that mounts each of the multiple sections, each section having an application specific set of optical systems, which correspond to the light source within a particular section e.g., each section houses excitation and emission filters, and a beam splitter for each different light source. The apparatus 12 additionally has a power source 44 and the multi-purpose cartridge 140 has a coupler 46 for providing a current supply to the multiple sections and light sources, such as light sources 18 and 116, from the power source 44 and is designed to be removably engaged with apparatus 12. According to the embodiment shown in FIGS. 6A and 6B, the power source 44 is coupled to light sources 18 and 116 by the coupler 46, as described with respect to FIGS. 1B and 1C. Inside the cartridge 140, between the cartridge plug and the light source control board 68 (shown in FIG. 2), the coupling continues with the help of a flat cable that coils up or uncoils again while the support 142 rotates.

As shown in FIGS. 6A and 6B, the multi-purpose cartridge 140 has a movable support 142 (e.g., a revolver-type mechanism), which mounts the first light source 18 and corresponding optics onto a first section 144 (i.e., a chamber) of the cartridge 140. The movable support 142 also mounts the second light source 116 and corresponding optics onto a second section 146 of the cartridge 140. The movable support 142 also mounts other sections e.g., sections 3, 4, 5, or more (not shown) onto the cartridge 140. A particular application provided by the first section 144 or second section 146, or other sections of the cartridge 140, (e.g., a particular wavelength of exciting light, as determined by the light source 18 or 116, or optical system for a luminescence application) is selected by moving the desired light source 18 or 116 into an operating position within the cartridge 140, e.g., by rotating a revolver mechanism of the movable support 142 about the axis (dotted line). FIG. 6A shows the operating position for the first light source 18 and FIG. 6B shows the operating position for the second light source 116.

Referring again to FIG. 6A, the first section 144 of the multi-color cartridge 140 comprises a first light source 18, which produces a first exciting light 20 (preferably collimated), and a first optical system 22, which has components, including a first excitation filter 24, for directing the first exciting light 20 to a partially reflecting mirror 148 and then to a dichroic beamsplitter 150 toward the read head 28. Prior to passing through the dichroic beamsplitter 150, a portion of the first exciting light 20 passes the partially reflecting mirror 148 and is measured by a detector 152, such as a photodiode, as previously described with respect to FIG. 2. The first exciting light 20 is directed to a sample 16 via a read head 28. The sample 16, containing the target 14, produces an emitting light 32. The first section 144 of the cartridge 140 has a second optical system 34, which receives the emitting light 32 from the read head 28 and directs the emitting light 32 from the sample 16 to the detector 36 via a filter 42, and a reflector 38, through the cartridge exit 40, which interfaces with the detector 36.

Referring again to FIG. 6B, the second section 146 of the multi-color cartridge 140 comprises a second light source 116, which produces a second exciting light 118 (preferably collimated), and a third optical system 154, which has components, including a first excitation filter 156, for directing the second exciting light 118 to a partially reflecting mirror 148 and then to the dichroic beamsplitter 158, and toward the read head 28. Prior to passing through the dichroic beamsplitter 158, a portion of the second exciting light 118 passes the partially reflecting mirror 148 and is measured by the detector 152, as previously described with respect to FIG. 2. The second exciting light 118 is directed to a sample 16 via a read head 28. The sample 16, containing the target 14, produces a second emitting light 160. The second section 146 of the cartridge 140 also has a fourth optical system 162, which receives the second emitting light 160 from the read head 28 and directs the second emitting light 160 from the sample 16 to the detector 36 via a filter 164, and the reflector 38, through the cartridge exit 40, which interfaces with the detector 36.

Referring now to FIG. 7, another embodiment of the apparatus 12 for analyzing a target 14 in a sample 16 is shown. According to the embodiment shown in FIG. 7, the apparatus 12 has a dual wavelength absorbance cartridge 170 that is equipped with first and second light sources 18 and 116, respectively. The apparatus 12 additionally has a power source 44 and the dual wavelength absorbance cartridge 170 has a coupler 46 for providing a current supply to light sources 18 and 116 from the power source 44. The dual wavelength absorbance cartridge 170 is designed to be removably engaged with apparatus 12.

As shown in FIG. 7, the dual wavelength absorbance cartridge 170 comprises first light source 18, which produces a first exciting light 20 (preferably collimated), and a first optical system 22, which has components, including a first excitation filter 24, for directing the first exciting light to a beam combiner 172 and then toward the sample 16. For absorbance applications, the beam is collimated to a smaller diameter than for fluorescence applications, and the excitation filters typically feature a smaller bandpass (i.e., narrower). For dual wavelength measurements, the dual wavelength absorbance cartridge 170 comprises a second light source 116, which produces a second exciting light 118, which is passed through a filter 124 and is aligned with the first exciting light 20 with help of the beam combiner 172 to produce a combined exciting light beam 174. The combined exciting light beam 174 is then passed through the cartridge support 52, via an aperture 176 (i.e., a window or light transparent section of the cartridge support 52) and focused into the sample 16, which is positioned on the sample support 17, via aperture 58. The dual wavelength measurement may be performed quasi simultaneously, by alternating the color of the combined beam 174, i.e., electronic switching between the first and second light sources 18 and 116. Emitting light 32 transmitted through the sample is collected by a read head 28 and focused onto an absorbance detector 178, containing, for example, a photodiode 38. Preferably, the signal measured at the photodiode 38 of the absorbance detector 178 is normalized with the beam intensity measured without the sample support 17. The signal is also normalized with respect to the light source monitoring circuitry, such as that described with respect to FIG. 2.

Referring now to FIG. 8, another embodiment of the apparatus 12 for analyzing a target 14 in a sample 16 is shown. According to the embodiment shown in FIG. 8, the apparatus 12 has a wide band light source cartridge 180 that is equipped with a first light source 18, which preferably is a wide band light source 182, such as a Xenon flash lamp module. The apparatus 12 additionally has a power source 44 and the wide band light source cartridge 180 has a coupler 46 for providing a current supply to light source 18 from the power source 44. The wide band light source cartridge 180 is designed to be removably engaged with apparatus 12.

The wide band light source 182 is a light source that can provide an exciting light over a wide band of the Ultraviolet (UV), visible (VIS), and near infrared (NIR) electromagnetic spectrum, (i.e., light having a wavelength from about 200 nm to about 1000 nm). Preferably, a Xenon flash lamp module is used as the wide band light source 182 because of the high intensity over the desired wavelength operating range. The flash mode is selected for its lower heat dissipation when compared with a constant Xenon Arc Discharge lamp.

According to the embodiment shown in FIG. 8, the wide band light source cartridge 180 comprises a first light source 18 includes a wide band light source 182. The wide band light source 182 produces an exciting light 20, which exits slit 184 of the wide band light source 182 and is directed (via a reflector 186) onto a wavelength selector 188, such as a monochromator grating that disperses the exciting light 20 (different wavelengths into different angles). A mirror 190 maps the different angles (wavelengths) onto different positions across the monochromator's exit slit 192, shown as a fan of rays indicated by dotted lines in FIG. 8. The wavelength of exciting light 198 (non dotted line) transmitted through the slit 192 is selected by rotating the wavelength selector 188. Further functions housed in the cartridge 180 are beam shaping optics 194, order sorting filters 196 (to remove unwanted contamination of the desired beam wavelength with light from other than first order grating diffraction), sitting on a filter wheel, and a partially reflecting mirror 64 and photodiode 62 for monitoring the intensity of the exiting beam, such as described with respect to FIG. 2. After exiting the wide band light source cartridge 180, the combined exciting light beam 198 is passed through the cartridge support 52 via aperture 176 and then focused onto the sample 16, which is positioned on the sample support 17, via aperture 58. Emitting light 32 transmitted through the sample 16 is collected by a read head 28 and focused onto an absorbance detector 178, such as a photodiode 38. Preferably, the signal measured at the photodiode 38 of the absorbance detector 178 is normalized with the beam intensity measured without the sample support 17. The signal is also normalized with respect to the light source monitoring circuitry, such as that described with respect to FIG. 2.

According to the present invention, any of the above described cartridges having an exciting light source, such as the cartridges shown in FIGS. 3-8 may be controlled by the electronic measurement circuitry 68 and corresponding detector 62, apparatus controller 74, and feedback loops 66 and 72 described with respect to FIG. 2.

Figure 9:
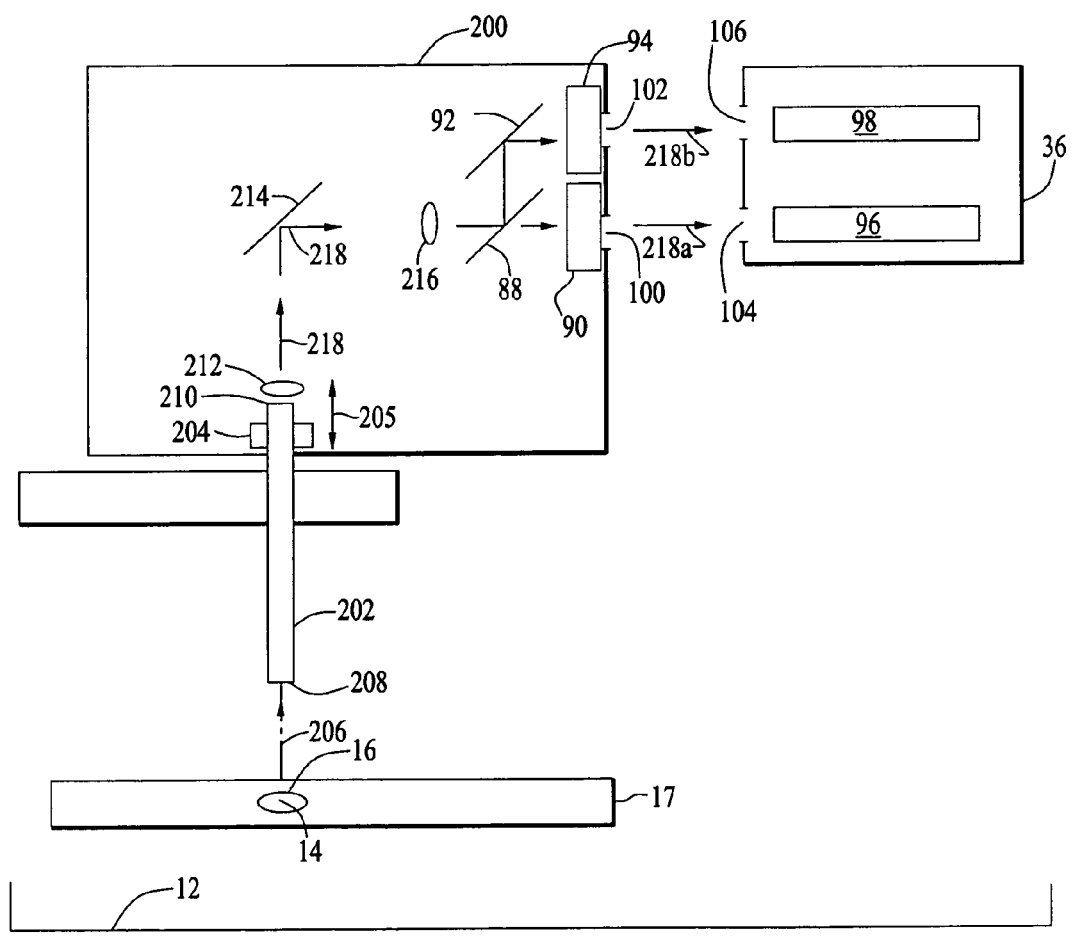
FIG. 9 is a schematic illustration of a luminescence cartridge, having an integrated read head, according to an embodiment of the present invention.

Referring now to FIG. 9, a luminescence cartridge 200 for use in an apparatus 12 for analyzing a target 14 in a sample 16 is shown. As shown in FIG. 9, the cartridge 200 comprises an integrated read head 202 and a driver 204, which moves the read head 202 in the direction indicated by arrow 205 into a detection position above the sample 16 when receiving emitting luminescent light 206 from the sample 16. The integrated read head 202 can also be moved by the driver 204 away from the sample 16 into a latent position when the luminescence cartridge 200 is not in use, or the apparatus 12 is being loaded with a new sample support 17. Preferably, the read head 202 is fully retractable into the cartridge 200, and also preferably, for reasons of saving measurement time, the read head 202 will not move up and down when moving from the one sample 16 to the next, but will stay in proximity above the sample support 17, when moving from one sample 16 to the next sample. The integrated read head 202 is retracted when the sample support 17 is moved in or out of the apparatus 12 in order to avoid parts of the sample support carrier (not shown) that extend beyond the upper sample support level.

Preferably, the integrated read head 202 is a rigid light guide that receives emitting luminescent light 206 at a proximal end 208 of the integrated read head 202 from a position above the sample holder 17 and sample 16. The emitting luminescent light 206 then exits the integrated read head 202 at a distal end 210 of the integrated read head 202 and is collimated by a lens 212 to produce a collimated light beam 218.

According to the embodiment of the luminescence cartridge 200 shown in FIG. 9, the apparatus 12 and luminescence cartridge 200 are configured for a bioluminescence resonance energy transfer (BRET) type measurement, where luminescence light is composed of two wavelength bands (e.g., a dual emission cartridge configuration) which is detected simultaneously with a dual channel detector. The dual emission cartridge and dual channel detector are further described with respect to FIGS. 3 and 4. As shown in FIG. 9, the collimated emitting luminescent light beam 218 is redirected with a reflector 214 toward a dichroic beamsplitter 88 via a lens 216 and separated into two wavelength bands 218*a* and 218*b*. The first wavelength band 218*a* is passed or transmitted by a beamsplitter 88 toward the detector 36 via a first emission filter 90 (e.g., a bandpass filter). The second wavelength band 218*b* is reflected by the beamsplitter 88, and reflected at the mirror 92 toward the detector 36 via a second emission filter 94 (e.g., a bandpass filter). The detector 36 is preferably a dual channel detector having two detectors 96 and 98 (e.g., photomultiplier tubes) stacked to form the dual channel detector. In addition, the luminescence cartridge 200 has a dual exit port 100 and 102, which is aligned with the detectors 96 and 98 via detector ports 104 and 106.

In an alternative embodiment, for a wider class of luminescence measurements, which do not require simultaneous measurement of two wavelength bands, the cartridge 200 may be simplified by omitting the beamsplitter 88, mirror 92, and second emission filter 94.

Figure 10:
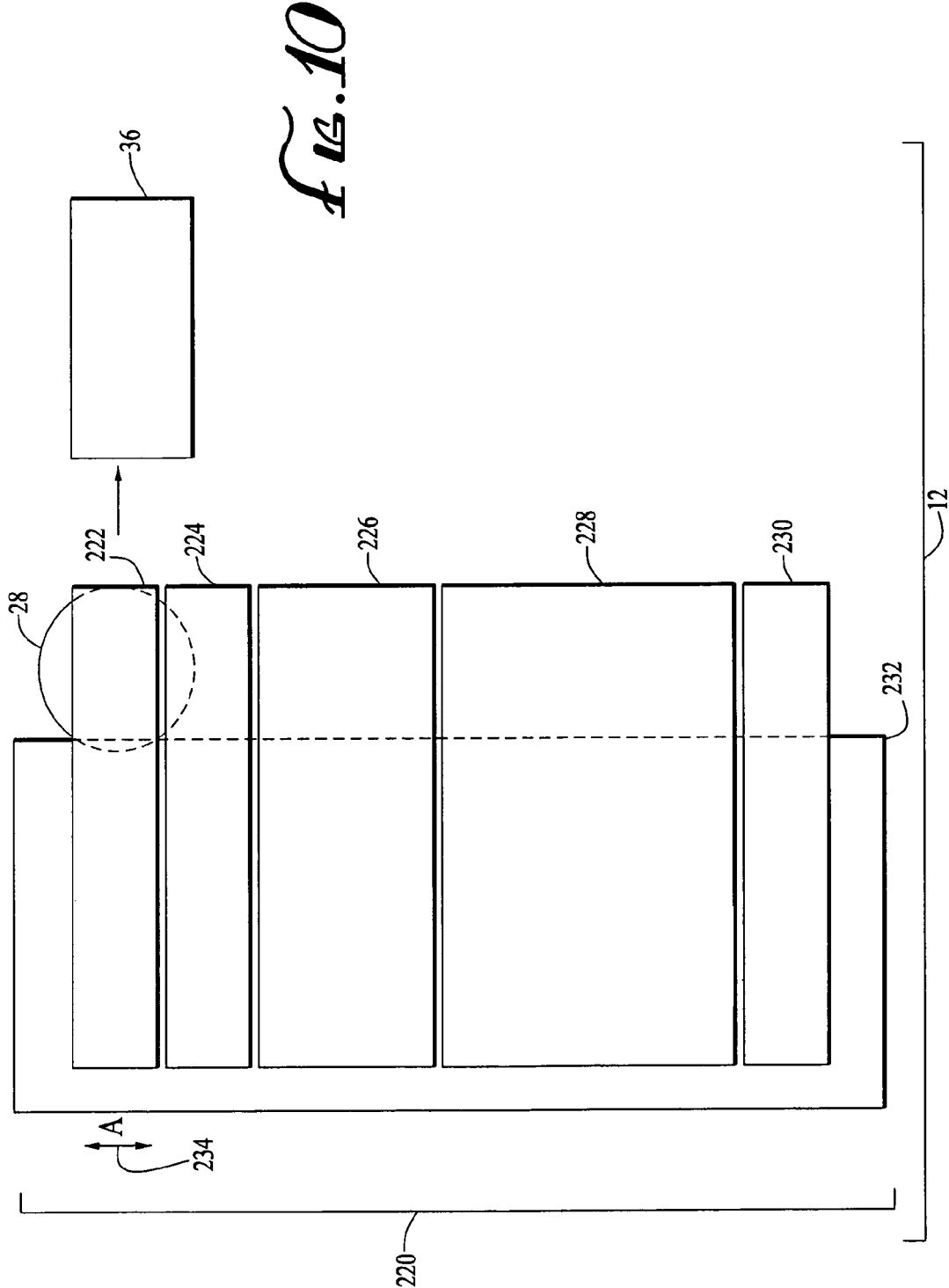
FIG. 10 is a schematic illustration of a top view of a cartridge system according to an embodiment of the present invention.

Referring now to FIG. 10, another embodiment of the invention, a cartridge system 220 for use in an apparatus 12 for analyzing a target in a sample (not shown) is provided. As shown in FIG. 10, the apparatus 12 has a cartridge support 232 (i.e., a slide mechanism or cartridge slider) which is configured to concurrently receive a multitude of different cartridges. According to this embodiment, a cartridge for a desired application, such as fluorescence, absorbance, or luminescence, is selected by the user and is selectively aligned by the apparatus 12 with the read head 28 and the detector 36 by moving the selected cartridge into the analysis position A, along the direction indicated by arrow 234. In this manner, a single instrument may house several application cartridges at a time and an application may be selected by the user without the user performing a multitude of application specific adjustments to the instrument such as selecting the correct combination and adjustment of filters, beamsplitters, apertures, and lightguides, etc. for a given application.

Referring again to FIG. 10, the cartridge system 220 comprises a plurality of cartridges, each cartridge being removably engaged with the apparatus 12. Examples of cartridges that may be used in the cartridge system 220 are one or more of the cartridges described in FIGS. 1-9. Exemplary cartridges used in the cartridge system 220 are shown in FIG. 10 as cartridge 222, cartridge 224, cartridge 226, cartridge 228, and cartridge 230. However, a greater or fewer number of cartridges may be used in the cartridge system 220 and the cartridges need not have the same dimensions such that cartridges having more complex systems (and larger dimensions) or less complex systems (and smaller dimensions) may be used in the apparatus 12. The apparatus 12 has a cartridge support 232 (i.e., a slide mechanism or cartridge slider) which is configured to receive the cartridges (e.g., cartridges 222, 224, 226, 228, and 230) and align each of the cartridges with the detector 36 and read head 28.

In a preferred but not required embodiment, each cartridge has indicia, such as an electrically erasable programmable read-only memory, EEPROM, that indicates the type of detection that the cartridge can be used for and the corresponding parameters for the particular cartridge. Also preferably, the cartridge support 232 features a cartridge detector, such as a data line function, or an electronic bus system, that enables the instrument control software (not shown) to identify a cartridge's slot position (i.e., the position of the cartridge on the cartridge support 232) and recognize any application specific parameters stored in the cartridge's EEPROM.

In another preferred but not required embodiment, the cartridge support 232 dimensions are such that it can be moved through a front door or access panel of the apparatus housing and every cartridge position or "slot" on the cartridge support 232 can be accessed for installation or removal of a cartridge. More preferably, one cartridge is capable of being removed from the cartridge support 232 and exchanged with a second cartridge, or alternately, a new cartridge is installed in an empty slot on the cartridge support 232 without the use of mechanical tools, or with a simple mechanical tool, such as for releasing a fastening mechanism (e.g., a fastening clip).

In another preferred but not required embodiment, at least one of the cartridges in the cartridge system 220 has one or more light sources that produces an exciting light, such as the cartridges described with respect to FIGS. 1-8. In another preferred but not required embodiment, at least one of the cartridges in the cartridge system 220 has an integrated read head and a driver (not shown), such as that described with respect to FIG. 9 for moving the read head.

Figure 11:
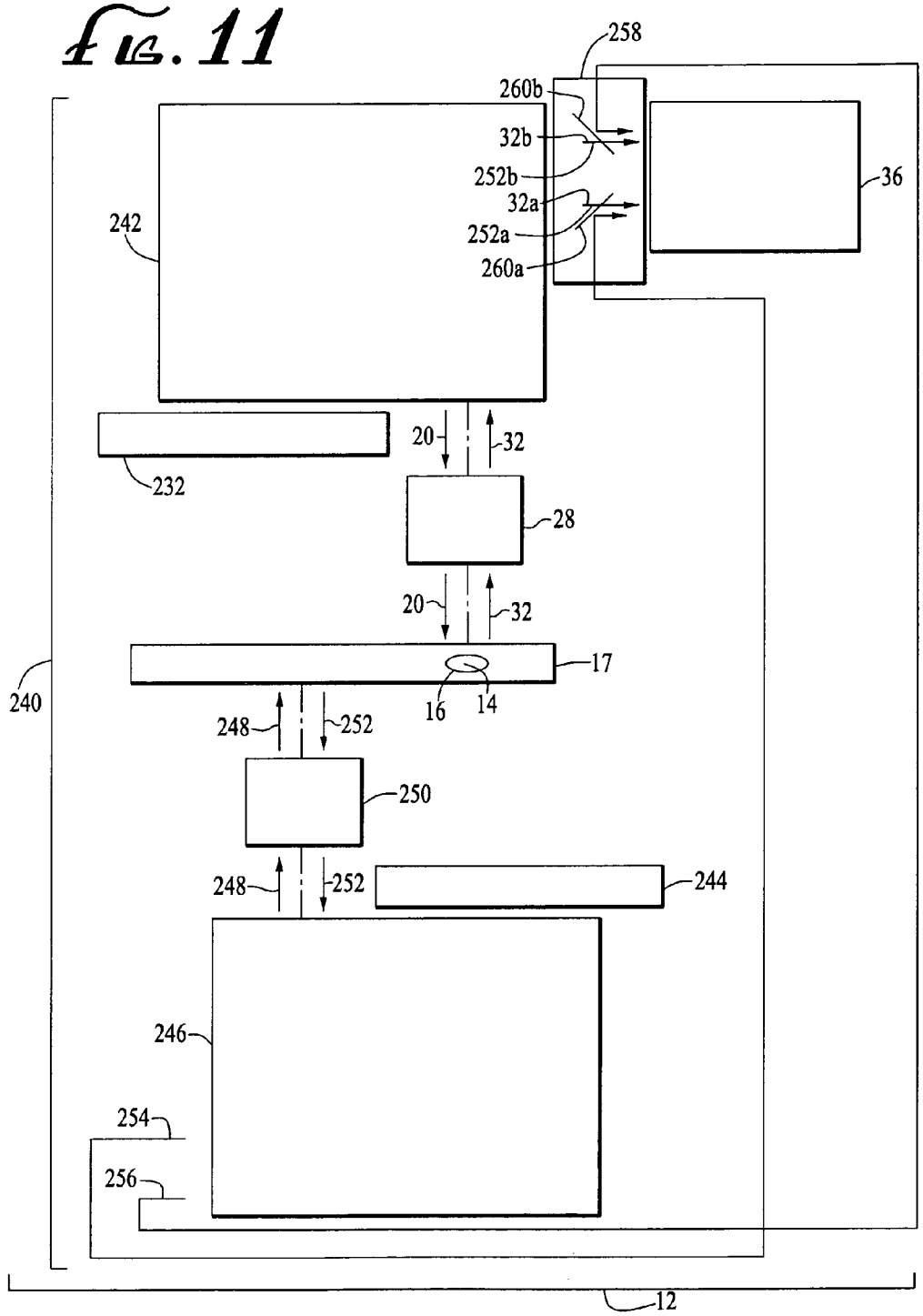
FIG. 11 is a schematic illustration of a top and bottom reading cartridge system according to an embodiment of the present invention.

Referring now to FIG. 11, another embodiment of the invention, a top and bottom reading cartridge system 240 for use in an apparatus 12 for analyzing a target 14 in a sample 16 is provided. As shown in FIG. 11, the apparatus 12 has a first cartridge support 232 which supports a first cartridge 242 and a second cartridge support 244 which supports a second cartridge 246. The first and second cartridges 242 and 246 may be any of those described herein such as the cartridges described with respect to FIGS. 1-9, but preferably are configured for fluorescence applications. As noted above in the description relating to FIGS. 1B and 1C, the first cartridge support 232 and/or the second cartridge support 244 may be configured for supporting a plurality of cartridges, and for selectively aligning one or more of the cartridges with the read head 28 or 250 and/or the detector 36, as appropriate for carrying out a particular type of measurement.

According to the embodiment shown in FIG. 11, the first cartridge support 232 and first cartridge 242 are positioned above the sample support 17. The exciting light 20 from the first cartridge 242 is directed to the sample 16 through a first read head 28. The emitting light 32 from the sample 16 is then directed again through the first cartridge 242, by which the emitting light 32 is directed to the detector 36 as previously described herein, for example, with respect to FIGS. 1-6. The emitting light 32 may be split into one or more wavelength bands 32a and 32b as previously described. The second cartridge support 244 and second cartridge 246 are positioned below the sample support 17 and the exciting light 248 from the second cartridge 246 is directed to the sample 16 through a second read head 250. The emitting light 252 is then directed again through the second cartridge 246, where it is split into emitting lights 252a and 252b and relayed remotely to the detector 36. Preferably, light guides 254 and 256 relay the emitting light 252a and 252b from the bottom of the second cartridge 246 through an exit port (not shown) to the detector 36.

The design of the first and second cartridges 242 and 246 is independent of whether the cartridge is positioned either above or below the sample support 17. However, when the cartridge configuration shown in FIG. 11 is used, a movable detector port support 258 (e.g., a slide or selector wheel mechanism) is used which switches the detector 36 from seeing either emitting light 32a and 32b from the first cartridge 242 and first read head 28 or seeing emitting light 252a and 252b from the second cartridge 246 and second read head 250. The emitting light 252a and 252b exiting the light guides 254 and 256 is reflected into the detector 36 by mirrors 260a and 260b. The selection between the first and second cartridges 242 and 246 is done by moving the movable detector port support 258 along an axis 262 perpendicular to the detector 36. This embodiment is further detailed in FIG. 12.

Figure 12:
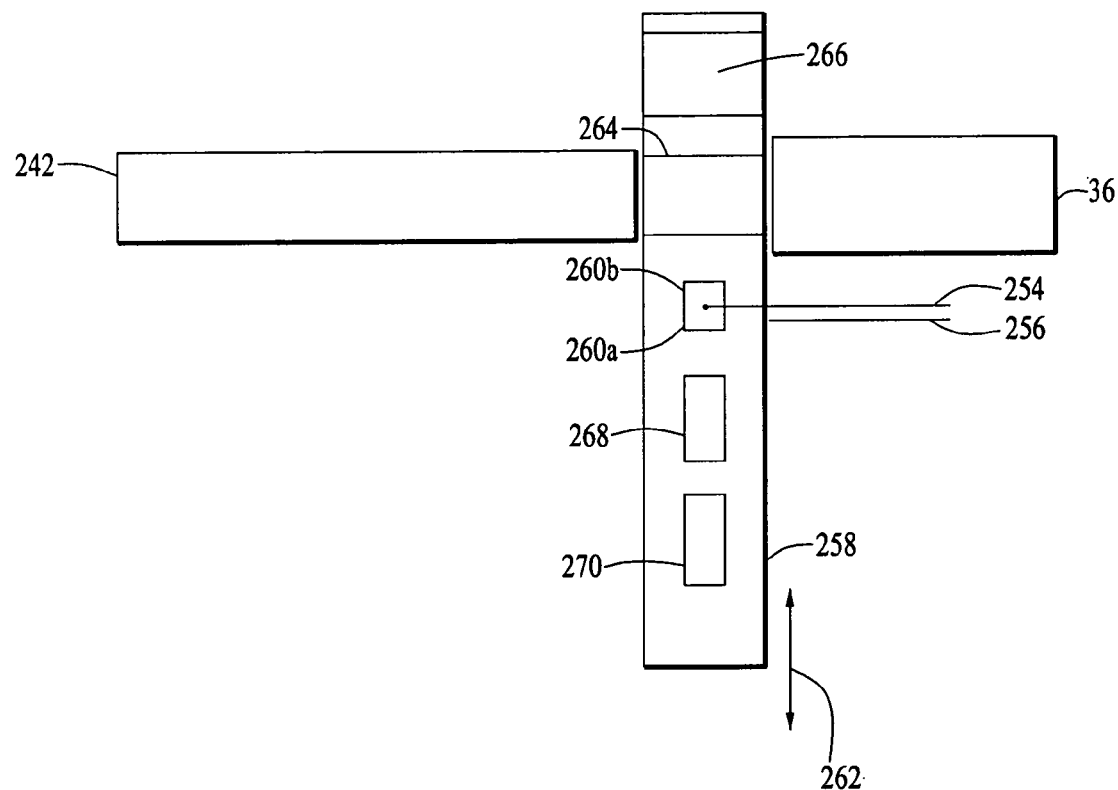
FIG. 12 is a schematic illustration of a top view of the cartridge configuration shown in FIG. 11.

According to the embodiment shown in FIG. 12, the movable detector port support 258 is located in the gap between the exit of the first cartridge 242 and the entrance to the detector 36. The movable detector port support 258 houses an aperture 264 (e.g., a beam pass) which directs emitting light 32a and 32b from the first cartridge 242 and a beam stop/ shutter 266 which protects the detector 36 when the instrument front door is opened, such as for maintenance or to exchange a cartridge. The movable detector port support 258 may also be equipped with light attenuating filters 268 and 270 which enable the system to analyze a signal that is too strong for the detector 36. The movable detector port support 258 may also be equipped with a constant low power light source in order to monitor the function and performance of the detector 36 over longer periods of operation (not shown). The light source resident in the detector port support 258 is built from a LED and stabilized by feedback from a photodiode, as described for a cartridge with respect to FIG. 2. The LED output is attenuated down to levels acceptable to the detector 36 by help of a diffusing glass. Another position along the movable detector port support 258 may house mirrors 260a and 260b that reflect the emitting light 252a and 252b exiting the light guides 256 and 254 from above and below the movable detector port support 258. Emitting light 252a and 252b exiting the light guides 256 and 254 can enter the detector 36 when the position of the light guides 256 and 254 on the detector port support 258 is aligned with the detector 36.

As is evident from FIGS. 2 and 8, in certain embodiments a removable cartridge may include a detector. As is also evident from FIGS. 1C, 7, 8 and 11, in certain embodiments systems implementing absorbance measurements such as illustrated in FIGS. 1C, 7 and 8 may be adapted to the top and bottom cartridge configuration illustrated in FIG. 11. As examples, the absorbance cartridge 10 shown in FIG. 1C, the dual wavelength absorbance cartridge 170 shown in FIG. 7, or the wide band light source absorbance cartridge shown in FIG. 8 may be loaded onto the second (bottom) cartridge support 244 shown in FIG. 11. In a further example, the absorbance detector 178 shown in FIGS. 7 and 8 may be provided in a removable cartridge that is loaded onto the first (upper) cartridge support 242 shown in FIG. 11. In such embodiments, the sample support 17, first cartridge support 242 and/or second cartridge support 244 may include apertures 58, 176 (FIGS. 7 and 8) as needed, and one or both read heads 28 and 250 may be bypassed as needed.

Figure 13:
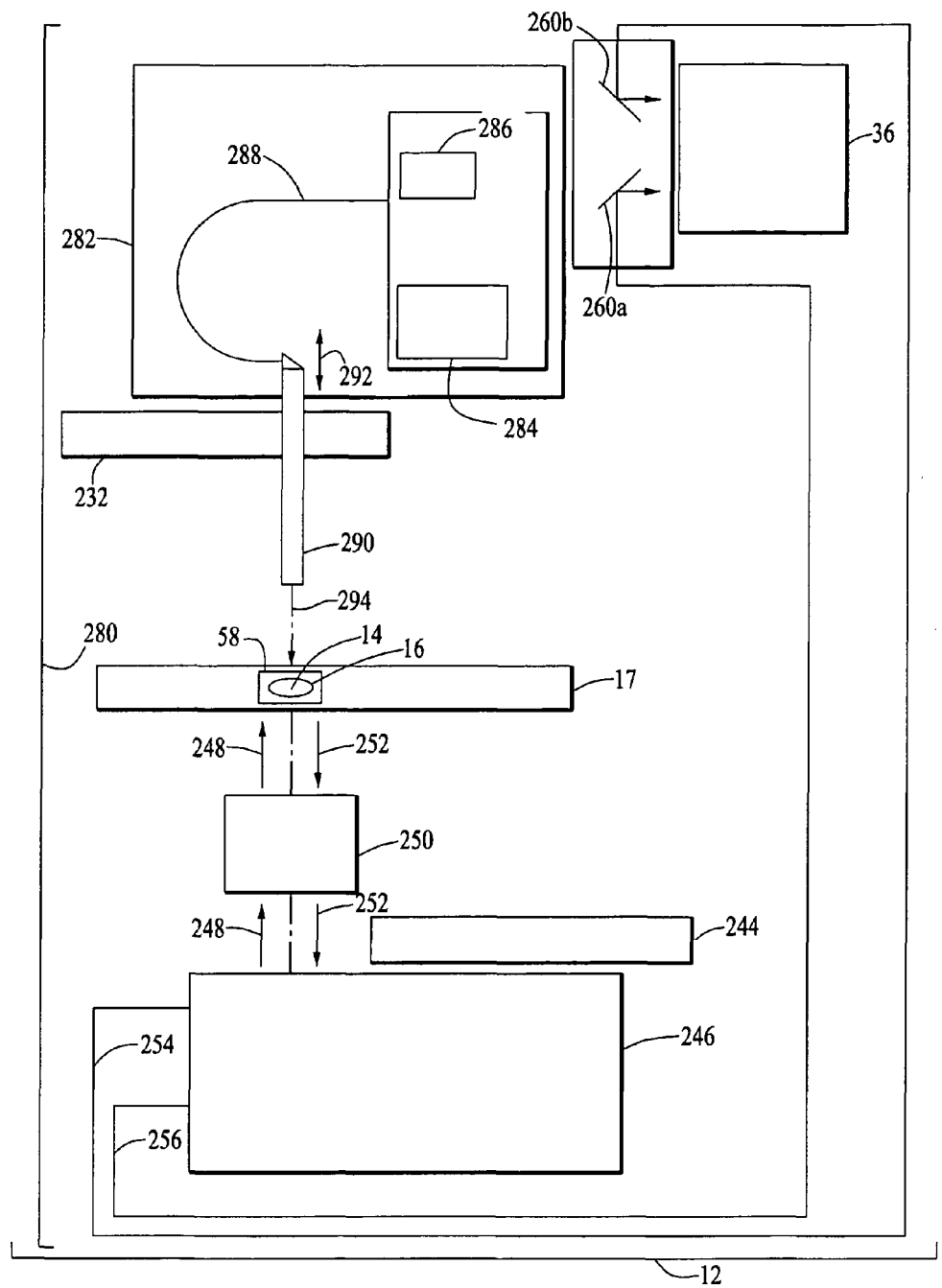
FIG. 13 is a schematic illustration of a flash fluorescence cartridge system according to an embodiment of the present invention.

Referring now to FIG. 13, another embodiment of the invention, a flash fluorescence cartridge system 280 for use in an apparatus 12 for analyzing a target 14 in a sample 16 is provided. The flash fluorescence cartridge system 280 has an injector cartridge (i.e., the first cartridge 282) that may be used for flash fluorescence applications, which require injection of a starter reagent in combination with immediate fluorescence reading.

For typical flash fluorescence applications, clear bottom microplates are frequently used as the sample support 17 (i.e., a sample support having an aperture 58) such that injection of the reagent occurs from above the well and fluorescence is measured simultaneously from below the sample holder 17. Accordingly, FIG. 13 uses the top and bottom reading cartridge configuration, which has been described with respect to FIG. 11. According to the embodiment shown in FIG. 13, an injector cartridge 282 is installed as the first cartridge (i.e., the upper cartridge) on the first cartridge support 232. A second cartridge 246 is positioned on a second cartridge support 244. The second cartridge 246 may be any of those described herein such as the cartridges described with respect to FIGS. 1-6 and 13, but configured for a fluorescence application. As noted again, the first cartridge support 232 and/or the second cartridge support 244 may be configured for supporting a plurality of cartridges, and for selectively aligning one or more of the cartridges with the read head 250 and/or the detector 36, as appropriate for carrying out a particular type of measurement.

As shown in FIG. 13, the first cartridge 282 features a reagent reservoir 284, a pump 286, and a tubing system 288 connected to a nozzle 290 (preferably rigid). The nozzle 290 can be driven down from within the first cartridge 282 to approach the sample support 17 from above, as shown by arrow 292. The nozzle 290 is aligned with a sample 16 and read head 250 and reagent 294 is delivered to the sample 16 via the nozzle 290. Exciting light 248 and emitting light 252 is directed to the sample 16 and subsequently to the detector 36 as described with respect to FIG. 11. Sample measurement may take place before, during, and after injection of reagent 294.

Using an injector module that can be easily removed under routine operating conditions, such as the injector cartridge described herein, provides several advantages. The injector cartridge and external docking station may also be used as a precision dispenser apparatus. In addition, the cartridge's tubing system can be easily rinsed/cleaned by the customer and primed, i.e., floated, thereby removing bubbles, with the reagent outside of the instrument enclosure. This may occur with the injector cartridge still plugged into the cartridge support, but with the cartridge support moved through the instrument door and having a waste reservoir placed underneath. Priming may also occur with the injector cartridge removed from the cartridge support and plugged into a docking station. Both strategies reduce the risk of accidentally floating the interior of the apparatus with reagent. Also, the output of the injector cartridge can be calibrated for the customer's solvents at the customer site using an external docking station mounted on top of weighing scales.

Figure 14:
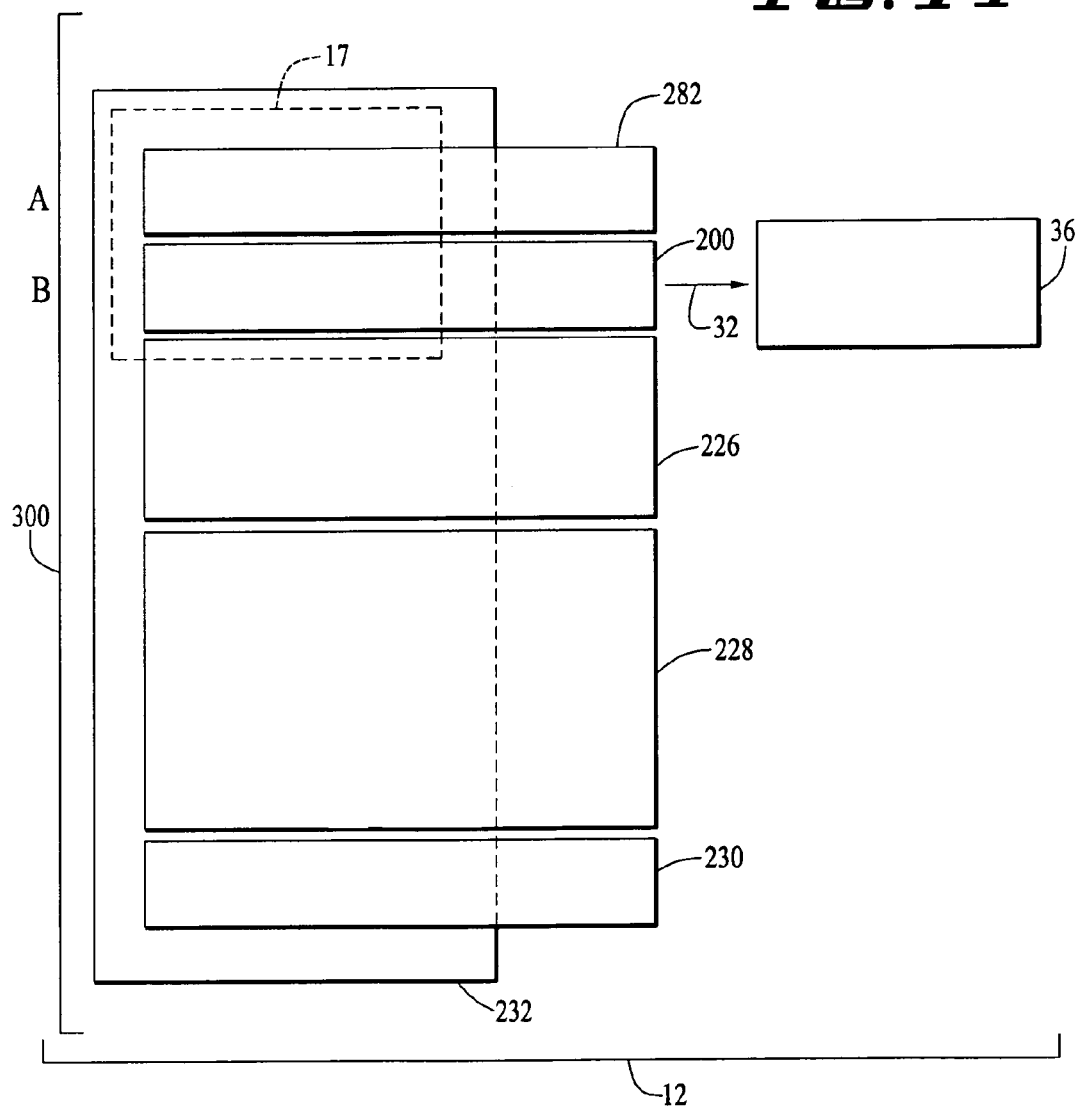
FIG. 14 is a schematic illustration of a top view of flash luminescence cartridge system according to an embodiment of the present invention.

Referring now to FIG. 14, another embodiment of the invention, a flash luminescence cartridge system 300, for use in an apparatus 12 for analyzing a target in a sample (not shown) is provided. Measurement of flash type luminescence requires the injection of a starter reagent, and measurement of luminescence light at a fraction of a second later. The configuration of the cartridge system 300 for this application has an injector cartridge 282, as described with respect to FIG. 13 and a luminescence cartridge 200 as described with respect to FIG. 9. The injector cartridge 282 and the luminescence cartridge 200 are positioned on adjacent slots on the cartridge support 232 as described with respect to FIG. 10. Any combination of cartridges may be possible (see for example FIG. 6). However, the cartridges are typically dedicated to a single (or only few) applications, unless the required performance would not be compromised by including an additional application. Preferably, due to the proximity of the injection position and the read position, the luminescence cartridge 200 and the injector cartridge 282 are fused into a single, dual slot cartridge.

As shown in FIG. 14, the luminescence cartridge 200 is aligned with the detector 36 and detects emitting light 32 from a first target 14a (not shown) on the sample support 17, which is positioned below the cartridge support 232. A flash type luminescence measurement is performed by first aligning the luminescence cartridge 200 with the detector 36 in the analysis position indicated in FIG. 14. The cartridge support 232 is then in a fixed position until the sample analysis is complete. The sample support 17 is then moved to align the first sample 16a (not shown) with the injector cartridge 282 in a first position, i.e., an "injecting position", position A. Starter reagent is then injected onto the first sample 16a. After the starter reagent is injected, the sample support 17 is then moved such that the first sample 16a on the sample support 17 is in a second position i.e., a "reading position", position B, where the first sample 16a is aligned with the luminescence read head (not shown) within the luminescence cartridge 200. A measurement may be taken on a second sample 16b (not shown) by moving the sample support 17 to the injecting position, i.e., the "injecting position", position A, below the injector cartridge 282 and injecting starter reagent onto the second sample 16b. The sample support 17 is then moved such that the second sample 16b on the sample support 17 is in the second position i.e., the "reading position", position B, where the second sample 16b is aligned with the luminescence read head (not shown) within the luminescence cartridge 200.

Figure 15A:
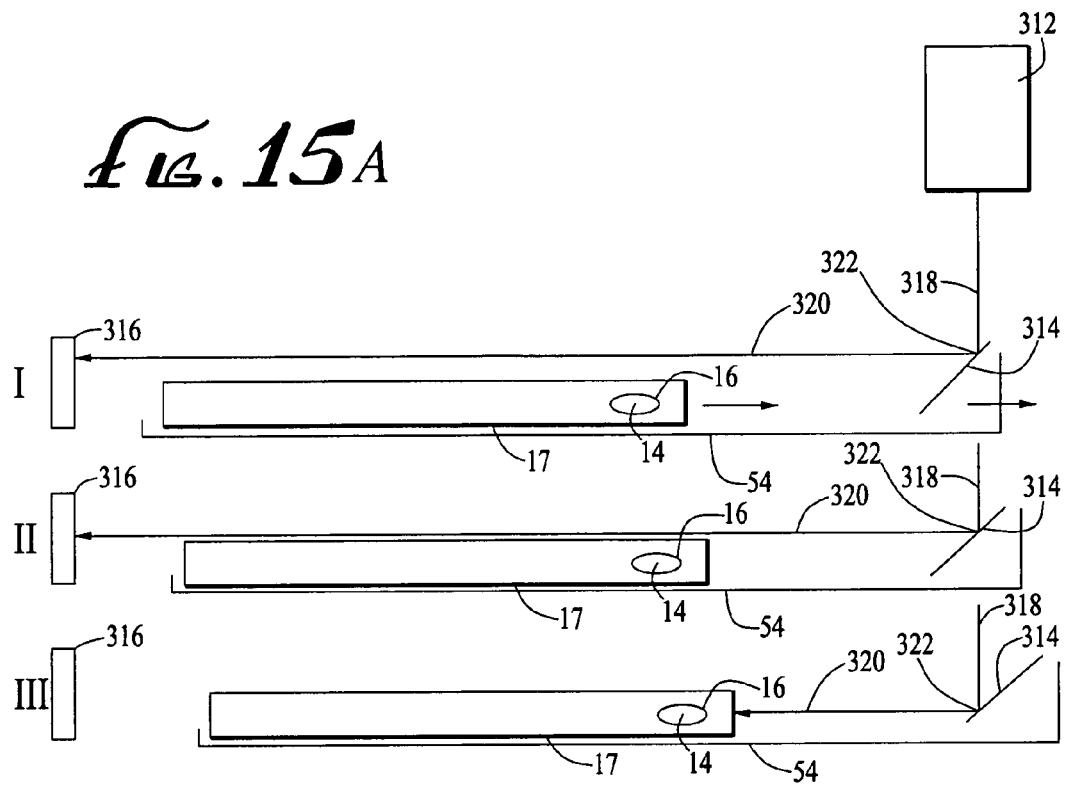
FIGS. 15A and 15B are a schematic illustration of a system for detecting the sample support clearance in a cartridge according to an embodiment of the present invention.
Figure 15B:
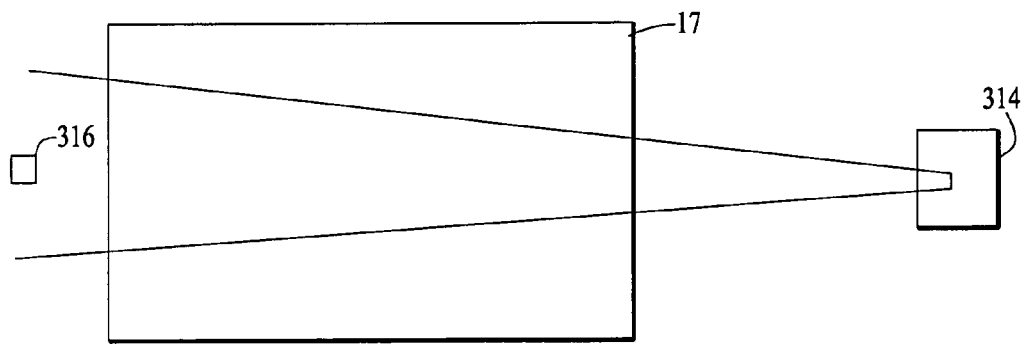

According to another preferred but not required embodiment of the invention, a sample support detector 310, for use in a system for analyzing a target 14 in sample 16 is shown in FIGS. 15A and 15B. As shown in FIG. 15A, a side view of the sample support detector 310, and FIG. 15B, a top view of the sample support detector 310, the sample support detector 310 comprises a detecting light source 312 (e.g., a laser pointer), a reflector 314 (e.g., a mirror) and a detector 316 (e.g., a photodiode). The sample support detector 310 measures the clearance (i.e., height) of the sample support 17 to avoid the luminescence read head or a fluorescence read head, which, when seeking to receive maximum signal from a sample may be moved down too far and thus collide with the top of the sample support 17. The result of the measurement produced by the sample support detector 310, is a value that instructs the software of the apparatus not to move lower than the particular value determined by the measurement.

According to the embodiment shown in FIGS. 15A and 15B, the detecting light source 312 produces a light beam 318, such as a laser line from a laser pointer, which is directed in the direction of the sample support 17. The reflector 314 is attached to the sample support carrier 54. Before reading the sample 16, the sample support carrier 54 is loaded with a sample 16 positioned on a sample support 17 outside the apparatus in a sample support loading position. To acquire a sample reading, the sample support carrier 54 must be retracted into the apparatus. On its way from the sample support loading position, outside the apparatus, to an inside initialization position, the sample support carrier 54 passes the detecting light source 312 Then, the light beam 318 is inflected (i.e., redirected) by the reflector 314 to produce an inflected light beam 320, which is parallel to the surface of the sample support 17, and then contacts the detector 316, as shown in FIG. 15A, view I. Then, the reflector 314 is moved such that the inflection point 322 of the light beam 318 on the reflector 314 moves down along the reflector surface until the inflected light beam 320 comes closer to the surface of the sample support 17, as shown in FIG. 15A, view II, and is further moved until the inflected light beam 318 is obstructed by the edge of the sample support 17, as shown in FIG. 15A, view III.

Preferably, as shown in FIG. 15A, the detecting light source 312 is positioned perpendicular to the sample support 17 and the reflector 314 redirects the light beam 318 at an angle of about 45 degrees so the inflected light beam 320 is approximately parallel to the sample support 17. Consequently, the signal at the photodiode undergoes an ON/OFF transition. By calibration using sample supports of different height, the position of the sample support 17 where the ON/OFF transition occurs is a measure of the height of the sample support 17.

As shown in FIG. 15B, alignment may be made less demanding by using a laser line pointer for the light beam 318 and projecting a fan of rays parallel to the surface of the sample support 17. The photodiode's sensitive area is extended in the direction orthogonal to the laser line projection (shown in FIG. 15B as vertical). Thereby, when not yet obstructed by the sample support 17, the fan of rays always has an intersection with the light detector 316.

Referring again to FIG. 5, according to another embodiment of the present invention, a method for fluorescence measurement using photoactivation of a functional group associated with a target 14 in a sample 16, the functional group being capable of changing from an inactivated state to an activated state in response to an exciting light is provided. According to this embodiment, first, a dual excitation cartridge 130 having first and second exciting light sources 116 and 18, respectively, which are capable of producing first and second exciting lights 118 and 20, respectively, is selected. Then, the first exciting light 118 is directed to the functional group associated with the target 14 in the sample 16, followed by directing the second exciting light 20 to the functional group associated with the target 14 in the sample 16. An emitting light 32 from the functional group associated with the target 14 is produced, and the emitting light 32 is directed to the detector 36 via the read head 28 and second optical system 34 in the cartridge 130. A signal that corresponds to the emitting light 32 is produced by the apparatus 12. A read-out may also be produced by the apparatus 12 which may be in a hard-copy or electronic form.

According to another embodiment of the present invention, a method for analyzing a target in a sample is provided. According to this embodiment, a cartridge system having a cartridge support and one or more cartridges that are removably engaged with a cartridge support is selected. The cartridges may be one or more of the cartridges described herein. Then, a first cartridge contained within the cartridge system is selected. A second cartridge, i.e., a new or replacement cartridge, not contained within the cartridge system is then selected. The first cartridge is then replaced with the second cartridge and a target in a sample is analyzed with the second cartridge. Preferably, the first cartridge may be removed from the apparatus and replaced with the second cartridge without the use of mechanical tools, and after the first cartridge is replaced with the second cartridge, the system is instructed, with apparatus-readable instructions, with information for analyzing the target in the sample.

According to another embodiment of the present invention, a method for analyzing a target in a sample or multiple samples is provided. According to this embodiment, first a cartridge system comprising first and second removable cartridges is selected. The first and second cartridges have one or more light sources that produce an exciting light, the exciting light produced from the first cartridge having a first wavelength, and the exciting light from the second cartridge having a second wavelength, the first and second wavelengths being different; and one or more supports configured to receive the first and second removable cartridges and align at least one of the removable cartridges with the detector and the read head. Then, a first sample to be analyzed is selected by aligning the first cartridge with the first sample, the detector, and read head. Preferably this is done by selecting the first cartridge and aligning the first cartridge with the read head and detector and then moving the first sample into an aligned position with the first cartridge. Then, the exciting light from the first cartridge is directed to the first target via the read head and a first emitting light from the first target is produced. The first emitting light from the first target is then directed to the detector and a first signal that corresponds to the first emitting light is produced. Then, the second cartridge is aligned with the first sample, the detector, and the read head. Preferably this is done by selecting the second cartridge and aligning the second cartridge with the read head and detector and then moving the first sample into an aligned position with the second cartridge. Then, the exciting light from the second cartridge is directed to the first target via the read head and a second emitting light from the first target is produced. The second emitting light from the first target is then directed to the detector and a second signal that corresponds to the second emitting light is produced. Preferably, the first and second emitting lights are directed from the first target to the detector via the read head and the first cartridge and second cartridge, respectively. The apparatus can also produce a read-out, such as a printed "hard copy" or electronic data of the first and second signals.

According to another embodiment, the method for analyzing a target in a sample or multiple samples further comprises analyzing a second target in a second sample, the second target being capable of generating third and fourth emitting lights in response to the exciting lights of the first and second wavelength. According to this embodiment, a second sample to be analyzed is selected. Then, the first cartridge is aligned with the second sample, the detector, and the read head, as previously described. Then, the exciting light from the first cartridge is directed to the second target via the read head and a third emitting light from the second target is produced. The third emitting light from the second target is then directed to the detector and a third signal that corresponds to the third emitting light is produced. The second cartridge is then aligned with the second sample, the detector, and the read head. The exciting light from the second cartridge is directed to the second target via the read head and a fourth emitting light from the second target is produced. The fourth emitting light is then directed from the second target to the detector and a fourth signal that corresponds to the fourth emitting light is produced. A read-out of the third and fourth signals may also be produced by the apparatus, as previously described, and/or a combined read-out of the first, second, third and fourth signals may be produced by the apparatus.

In the method described above, the order of sample analysis described as the first sample is initially analyzed by the first cartridge and then the second cartridge, and then the second sample is subsequently analyzed by the first cartridge and then the second cartridge. However, the invention is not limited to the order of sample analysis described above, as will be understood by those of skill in the art by reference to this disclosure. Further, for time saving in sample analysis, it is preferable to align the first cartridge with the detector and read head and complete the analysis of all the samples using the first cartridge in sequence, by moving the position of the samples relative to the first cartridge, such as by moving the samples on a microplate scanning stage. After all the samples have been analyzed with the first cartridge, the second cartridge may then be aligned with the detector and read head and the same, or additional samples may be analyzed.

Although the present invention has been discussed in considerable detail with reference to certain preferred embodiments, other embodiments are possible. Therefore, the scope of the appended claims should not be limited to the description of preferred embodiments contained herein.

What is claimed is:

1. A system for analyzing a target in a sample, the target being capable of generating an emitting light in response to an exciting light, the system comprising:
   a housing;
   a power source disposed in the housing;
   a detector disposed in the housing;
   a plurality of removable cartridges, at least one removable cartridge comprising a light source for producing an exciting light, a coupler for providing power to the light source from the power source, and a first optical system for directing the exciting light to the target;

a read head configured for receiving the emitting light from the target;

a movable sample carrier configured for aligning the sample with the read head; and a cartridge support movable in the housing and comprising a plurality of cartridge positions configured to receive the plurality of removable cartridges concurrently, the cartridge support configured to selectively align one or more of the removable cartridges with at least one of the detector and the read head, wherein each removable cartridge is removable from the cartridge support and exchangeable at the cartridge support with another cartridge.

2. The system according to claim 1, wherein the read head is configured for directing the emitting light from the target to the at least one removable cartridge, and the at least one removable cartridge further comprises a second optical system for receiving the emitting light from the read head and directing the emitting light to the detector.

3. The system of claim 1, wherein the plurality of removable cartridges further comprises an injector cartridge for injecting a reagent into the sample.

4. The system of claim 3, wherein the injector cartridge comprises a reagent reservoir, a pump, and a movable nozzle that is movable toward the target from within the injector cartridge.

5. The system of claim 1, wherein the at least one removable cartridge further comprises a light source detector for monitoring the intensity of the exciting light.

6. The system of claim 1, wherein the detector comprises a dual channel light detector.

7. The system of claim 1, further comprising a sample support detector configured for detecting a sample support loaded on the sample carrier.

8. The system of claim 7 wherein the sample support detector comprises a detecting light source, a reflector and a light source detector.

9. A system for analyzing a target in a sample, the target being capable of generating an emitting light in response to an exciting light, the system comprising:

a housing;

a power source disposed in the housing;

a detector disposed in the housing;

a sample carrier for supporting the sample in the housing;

a first removable cartridge comprising a reagent reservoir, a pump, and a movable nozzle for injecting a reagent into the sample;

a first cartridge support configured to receive the first removable cartridge and move the nozzle into alignment with the sample;

a second removable cartridge comprising a light source for providing an exciting light, a coupler for providing power to the light source from the power source, and a first optical system for directing the exciting light to the target;

a second cartridge support configured to receive the second removable cartridge; and a read head configured for directing the exciting light from the second removable cartridge to the target, wherein the second cartridge support is configured for moving the second removable cartridge into alignment with the read head.

10. The system of claim 1, wherein the read head is positioned between the sample carrier and a selected one of the removable cartridges.

11. The system of claim 1, wherein the read head is further configured for directing the exciting light from the at least one removable cartridge to the target.

12. The system of claim 1, wherein the light source comprises a first light source and a second light source, the at least one removable cartridge further comprises a movable support to which the first light source and the second light source are mounted, and the movable support is configured for moving the first light source and the second light source to a selected position for directing exciting light from the first light source or the second light source to the target.

13. The system of claim 1, wherein the read head is positioned between the sample carrier and the detector and is further configured for directing the emitting light to the detector.

14. The system of claim 13, wherein the light source comprises a first light source for producing a first exciting light at a first wavelength, and a second light source for producing a second exciting light at a second wavelength.

15. The system of claim 13, wherein the light source comprises a wide band light source, and the first optical system comprises a wavelength selector.

16. The system of claim 1, wherein the read head is separate from the plurality of removable cartridges.

17. The system of claim 1, wherein the read head is integrated with at least one of the removable cartridges, and the removable cartridge with which the read head is integrated further comprises a driver configured for moving the read head toward the target.

18. The system of claim 1, wherein the light source comprises a first light source for producing a first exciting light and a second light source for producing a second exciting light.

19. The system of claim 1, wherein the plurality of removable cartridges further comprises an additional cartridge, and the additional cartridge is selected from the group consisting of a fluorescence cartridge, an absorbance cartridge, a luminescence cartridge, and an injector cartridge.

20. The system of claim 1, wherein the sample carrier is configured for supporting a sample support containing a plurality of samples, and for sequentially moving one or more selected samples into alignment with the read head.

21. The system of claim 1, wherein the cartridge support configured to receive the plurality of removable cartridges is a first cartridge support configured to receive a plurality of first removable cartridges, and further comprising a second cartridge support configured to receive a second removable cartridge.

22. The system of claim 21, wherein the sample carrier is positioned between the first cartridge support and the second cartridge support.

23. The system of claim 21, wherein the light source of the at least one removable cartridge of the plurality of first removable cartridges is a first light source for producing a first exciting light, and further comprising a second removable cartridge engaged with the second cartridge support, the second removable cartridge comprising a second light source for producing a second exciting light and a second optical system for directing the second exciting light to the target.

24. The system of claim 23, wherein the target is capable of generating a first emitting light in response to the first exciting light and a second emitting light in response to the second exciting light, and further comprising a second read head configured for directing the second emitting light from the target to the second removable cartridge, and a third optical system configured for directing the second emitting light from the second removable cartridge to the detector.

25. The system of claim 24, wherein the third optical system comprises a dual light guide.

26. The system of claim 24, comprising a detector port, wherein the detector port is switchable between directing the first emitting light to the detector and directing the second emitting light to the detector.

27. The system of claim 21, wherein the second cartridge support comprises a plurality of cartridge positions configured to receive a plurality of second removable cartridges concurrently.

28. The system of claim 1, wherein the cartridge support comprises a cartridge detector.

29. The system of claim 28, wherein each of the plurality of removable cartridges comprises an indicia indicating the type of detection the removable cartridge can be used for, and the cartridge detector is configured for detecting the indicia.

30. The system of claim 29, wherein the indicia is an electrically erasable programmable read-only memory.

31. The system of claim 28, wherein the cartridge detector is configured for identifying the position of one or more of the removable cartridges on the cartridge support.

32. The system of claim 3, wherein the sample carrier is movable between an injecting position and a reading position, wherein at the injecting position the sample carrier aligns the target with the injector cartridge, and at the reading position the sample carrier aligns the sample with the at least one removable cartridge.

33. The system of claim 6, wherein the light source comprises a first light source for producing a first exciting light and a second light source for producing a second exciting light.

34. The system of claim 9, wherein the read head is configured for directing the emitting light from the target to the second removable cartridge, and the second removable cartridge further comprises a second optical system configured for receiving the emitting light from the read head and directing the emitting light from the read head to the detector.

35. The system of claim 9, wherein the detector comprises a dual channel light detector.

36. The system of claim 9, wherein at least one of the first cartridge support and the second cartridge support comprises a plurality of cartridge positions configured to receive a plurality of removable cartridges concurrently, and the at least one cartridge support is configured to selectively align one or more of the removable cartridges with at least one of the detector and the read head.

37. The system of claim 9, further comprising a second optical system configured for directing the emitting light to the detector.

38. The system of claim 37, wherein the second optical system comprises a light guide.

39. The system of claim 9, wherein the sample carrier is positioned between the first cartridge support and the second cartridge support.

40. The system of claim 39, wherein the sample carrier is configured for supporting a sample support containing a plurality of samples, and for sequentially moving one or more selected samples into alignment with the read head.

41. A system for analyzing a target in a sample, the target being capable of generating a luminescent light, the system comprising:
a housing;
a read head configured for receiving luminescent light from the target;
a detector disposed in the housing and configured for detecting the luminescent light;
a sample carrier configured for aligning the sample with the read head;
a plurality of removable cartridges, wherein at least one of the removable cartridges is a luminescence cartridge comprising an optical system configured for directing the luminescent light from the read head to the detector, the optical system comprising a collimating lens; and
a cartridge support movable in the housing and comprising a plurality of cartridge positions configured to receive the plurality of removable cartridges concurrently, the cartridge support configured to selectively align one or more of the removable cartridges with at least one of the detector and the read head, wherein each removable cartridge is removable from the cartridge support and exchangeable at the cartridge support with another cartridge.

42. The system of claim 41, comprising a sample carrier configured for supporting the sample in alignment with the read head.

43. The system of claim 41, wherein the sample carrier is configured for supporting a sample support containing a plurality of samples, and for sequentially moving one or more selected samples into alignment with the read head.

44. The system of claim 41, wherein the read head is integrated with the luminescence cartridge, and the luminescence cartridge comprises a driver configured for moving the read head toward the target.

45. The system of claim 41, wherein the detector comprises a dual channel detector.

46. The system of claim 45, wherein the optical system comprises a beam splitter configured for splitting the luminescent light into at least a first wavelength band and a second wavelength band, and the detector is configured for respectively receiving the first wavelength band and the second wavelength band.

47. The system of claim 41, wherein the plurality of removable cartridges comprises an injector cartridge for injecting a reagent into the sample.

48. The system of claim 47, wherein the sample carrier is movable between an injecting position and a reading position, wherein at the injecting position the sample carrier aligns the sample with the injector cartridge, and at the reading position the sample carrier aligns the sample with the luminescence cartridge.

49. The system of claim 47, wherein the injector cartridge comprises a reagent reservoir, a pump, and a nozzle movable toward the sample from within the injector cartridge.

50. The system of claim 41, wherein at least one of the removable cartridges comprises a light source for producing an exciting light, the read head is further configured for directing the exciting light to the target, and the target is associated with a functional group capable of changing from an inactivated state to an activated state in response to photoactivation by the exciting light.

51. A system for analyzing a target in a sample, the target being capable of generating an emitting light, the system comprising:
a housing;
a detector attached to the housing;
a first read head;
a second read head;
a sample carrier interposed between the first read head and the second read head and configured for selectively aligning the sample with the first read head and the second read head;

a first removable cartridge selected from the group consisting of a fluorescence cartridge comprising a light source, a luminescence cartridge comprising a collimating lens, an absorbance cartridge comprising a light source, and an absorbance cartridge comprising an absorbance detector;

a first cartridge support disposed above the sample carrier, and configured to receive the first removable cartridge and align the first removable cartridge with at least one of the first read head and the detector; and a second cartridge support disposed below the sample carrier, and configured to receive a second removable cartridge and align the second removable cartridge with at least one of the second read head and the detector.

52. The system of claim 51, wherein the first removable cartridge comprises a first light source for producing a first exciting light and a first optical system configured for directing the first exciting light to the target, and the first read head is configured for directing the first exciting light from the first optical system to the target.

53. The system of claim 52, wherein the target is capable of generating a first emitting light in response to the first exciting light, the first read head is further configured for directing the first emitting light from the target to the first removable cartridge, and the first removable cartridge further comprises a second optical system configured for directing the first emitting light from the first read head to the detector.

54. The system of claim 53, further comprising a second removable cartridge engaged with the second cartridge support, the second removable cartridge comprising a second light source for producing a second exciting light and a third optical system configured for directing the second exciting light to the target, wherein the second read head is configured for directing the second exciting light from the third optical system to the target.

55. The system of claim 54, wherein the target is capable of generating a second emitting light in response to the second exciting light, the second read head is further configured for directing the second emitting light from the target to the second removable cartridge, and the second removable cartridge further comprises a fourth optical system configured for directing the second emitting light from the second read head to the detector.

56. The system of claim 52, wherein the target is capable of generating a first emitting light in response to the second exciting light and a second emitting light in response to the second exciting light, and further comprising:

a second removable cartridge engaged with the second cartridge support, the second removable cartridge comprising a second light source for producing the second exciting light and a second optical system configured for directing the second exciting light to the target, wherein the second read head is configured for directing the second exciting light from the second optical system to the target; and a third optical system configured for directing the second emitting light from the second removable cartridge to the detector.

57. The system of claim 56, wherein the third optical system comprises a light guide.

58. The system of claim 52, wherein the target is capable of generating a first emitting light in response to the second exciting light and a second emitting light in response to the second exciting light, and further comprising:

a second removable cartridge engaged with the second cartridge support, the second removable cartridge comprising a second light source for producing the second exciting light and a second optical system configured for directing the second exciting light to the target, wherein the second read head is configured for directing the second exciting light from the second optical system to the target; and a detector port switchable between directing a first emitting light from the first removable cartridge to the detector and directing a second emitting light from the second removable cartridge to the detector.

59. The system of claim 58, further comprising a shutter movable to a position in front of the detector port.

60. The system of claim 58, further comprising one or more attenuating filters movable to a position in front of the detector port.

61. The system of claim 58, further comprising another light source movable to a position in front of the detector port to verify detector function.

62. The system of claim 58, wherein the detector port communicates with a third optical system configured for directing the second emitting light from the second removable cartridge to the detector port.

63. The system of claim 61, wherein the first removable cartridge is a luminescence cartridge, and the luminescence cartridge further comprises a third read head integrated with the luminescence cartridge and configured for directing a luminescent light from the target to the detector, and a driver configured for moving the third read head toward the target.

64. The system of claim 63, wherein the detector comprises a dual channel detector.

65. The system of claim 64, wherein the optical system comprises a beam splitter configured for splitting the luminescent light into at least a first wavelength band and a second wavelength band, and the detector is configured for respectively receiving the first wavelength band and the second wavelength band.

66. The system of claim 63, wherein the luminescence cartridge comprises a light source for producing an exciting light, and the third read head is further configured for directing the exciting light to the target, the target being associated with a functional group capable of changing from an inactivated state to an activated state in response to photoactivation by the exciting light.

67. The system of claim 51, further comprising a second removable cartridge engaged with the second cartridge support, the second removable cartridge comprising a light source for producing an exciting light and an optical system configured for directing the exciting light to the target, the target being capable of generating the emitting light in response to the exciting light, wherein the first read head is configured for receiving the emitting light from the target.

68. The system of claim 67, wherein the light source comprises a first light source for producing a first exciting light at a first wavelength, and a second light source for producing a second exciting light at a second wavelength.

69. The system of claim 67, wherein the light source comprises a wide band light source, and the first optical system comprises a wavelength selector.

70. The system of claim 67, wherein the first removable cartridge is an absorbance cartridge comprising an absorbance detector, and the read head is configured for directing the emitting light to the absorbance cartridge.

71. The system of claim 51, wherein the sample carrier is configured for supporting a sample support containing a plurality of samples, and for sequentially moving one or more selected samples into alignment with at least one of the first read head and the second read head.

72. The system of claim 51, wherein at least one of the first cartridge support and the second cartridge support comprises a plurality of cartridge positions configured to receive a plurality of removable cartridges concurrently, and the at least one cartridge support is configured to selectively align one or more of the removable cartridges with at least one of the detector, the first read head and the second read head.

* * * * *